(12) United States Patent
Kapoor et al.

(10) Patent No.: US 10,888,577 B2
(45) Date of Patent: Jan. 12, 2021

(54) MIRNA BIOMARKERS FOR CARTILAGE DEGENERATION

(71) Applicant: UNIVERSITY HEALTH NETWORK, Toronto (CA)

(72) Inventors: Mohit Kapoor, Toronto (CA); Akihiro Nakamura, Toronto (CA); Raja Rampersaud, Toronto (CA)

(73) Assignee: UNIVERSITY HEALTH NETWORK, Toronto (CA)

(*) Notice: Subject to any disclaimer, the term of this patent is extended or adjusted under 35 U.S.C. 154(b) by 10 days.

(21) Appl. No.: 16/079,405

(22) PCT Filed: Jan. 31, 2017

(86) PCT No.: PCT/CA2017/000019
§ 371 (c)(1),
(2) Date: Aug. 23, 2018

(87) PCT Pub. No.: WO2017/143430
PCT Pub. Date: Aug. 31, 2017

(65) Prior Publication Data
US 2019/0008885 A1 Jan. 10, 2019

Related U.S. Application Data

(60) Provisional application No. 62/299,305, filed on Feb. 24, 2016.

(51) Int. Cl.
| | |
|---|---|
| *C07H 21/04* | (2006.01) |
| *A61K 31/7088* | (2006.01) |
| *A61K 45/06* | (2006.01) |
| *C12N 15/113* | (2010.01) |
| *A61P 19/02* | (2006.01) |
| *G01N 33/574* | (2006.01) |

(52) U.S. Cl.
CPC .......... *A61K 31/7088* (2013.01); *A61K 45/06* (2013.01); *A61P 19/02* (2018.01); *C12N 15/113* (2013.01); *G01N 33/57488* (2013.01); *A61K 2300/00* (2013.01); *C12N 2310/141* (2013.01); *C12N 2320/10* (2013.01); *G01N 2800/105* (2013.01); *G01N 2800/50* (2013.01); *G01N 2800/56* (2013.01)

(58) Field of Classification Search
None
See application file for complete search history.

(56) References Cited

FOREIGN PATENT DOCUMENTS

| WO | WO 2008/057234 | 5/2008 |
|---|---|---|
| WO | WO 2009/091972 | 7/2009 |

OTHER PUBLICATIONS

Endisha, Helal, et al. "The complex landscape of microRNAs in articular cartilage: biology, pathology, and therapeutic targets." JCI insight 3.17 (2018).*
Chu, Chen, et al. "Transcriptional information revealed differentially expressed circular RNAs in facet joint osteoarthritis." Biochemical and biophysical research communications 497.2 (2018): 790-796.*
Agarwal, et al., "Role of NF-κβ Transcription Factors in Anti-Inflammatory and Proinflammatory Actions of Mechanical Signals," *Arthritis & Rheumatism*, 50: 3541-3548, 2004.
An, et al., "From Moderately Severe to Severe Hypertriglyceridemia Induced Acute Pancreatitis: Circulating miRNAs Play Role as Potential Biomarkers," *PloS One*, 9(11): e111058, 2014.
Anderson, et al., "A Role for Dicer in Aging and Stress Survival," *Cell Metabolism*, 16: 285-286, 2012.
Bauge, et al., "Interleukin-1Beta Up-Regulation of Smad7 Via NR-KappaB Activation in Human Chondrocytes," *Arthritis & Rheumatism*, 58: 221-226, 2008.
Beg, et al., "I Kappa B Interacts with the Nuclear Localization Sequences of the Subunits of NF-Kappa B: A Mechanism for Cytoplasmic Retention," *Genes & Development*, 6: 1899-1913, 1992.
Beyer, et al., "Signature of Circulating microRNAs in Osteoarthritis," *Annals of the Rheumatic Diseases*, 74(3): e18, 2015.
Brown, et al., "NAVIGaTOR: Network Analysis, Visualization and Graphing Toronto," *Bioinformatics*, 25: 3327-3329, 2009.
Castoldi, et al., "A Sensitive Array for microRNA Expression Profiling (miChip) Based on Locked Nucleic Acids (LNA)," *RNA*, 12(5): 913-920, 2006.
Gabler, et al., "Stage-Specific miRs in Chondrocyte Maturation: Differentiation-Dependent and Hypertrophy-Related miR Clusters and the miR-181 Family," *Tissue Engineering: Part A*, 21(23-24): 2840-2851, 2015.
Iliopoulos, et al., "STAT3 Activation of miR-21 and miR-181b-1 via PTEN and CYLD are Part of the Epigenetic Switch Linking Inflammation to Cancer," *Mol Cell*, 39: 493-506, 2010.
International Search Report and Written Opinion Issued in Corresponding PCT Application No. PCT/CA2017/000019, dated May 15, 2017.
Johnnidis, et al., "Regulation of Progenitor Cell Proliferation and Granulocyte Function by microRNA-223," *Nature*, 451: 1125-1129, 2008.
Kastrati, et al., "PHLDA1 Expression is Controlled by an Estrogen Receptor-NFKappaB-miR-181 Regulatory Loop and is Essential for Formation of ER+Mammospheres," *Oncogene*, 34: 2309-2316, 2015.
Lee, et al., "MicroRNA Maturation: Stepwise Processing and Subcellular Localization," The *Embo Journal*, 21: 4663-4670, 2002.
Lee, et al., "The Nuclear RNAse Drosha Initiates microRNA Processing," *Nature*, 425: 415-419, 2003.
Li, et al., "miR-146a, an IL-1β Responsive miRNA, Induces Vascular Endothelial Growth Factor and Chondrocyte Apoptosis by Targeting Smad4," *Arthritis Research & Therapy*, 14: R75, 2012.

(Continued)

*Primary Examiner* — Kimberly Chong
(74) *Attorney, Agent, or Firm* — Norton Rose Fulbright US LLP

(57) ABSTRACT

There is disclosed herein methods, uses and systems for the detection, diagnosis, prognosis, treatment or prevention of a disease or condition comprising cartilage degeneration in a subject that is in need thereof. The methods comprise the use, inhibition or measurement of at least one of miR-181 a-5p and miR-4454, in the subject.

6 Claims, 15 Drawing Sheets

Specification includes a Sequence Listing.

(56) References Cited

OTHER PUBLICATIONS

Londin, et al., "Analysis of 13 Cell Types Reveals Evidence for the Expression of Numerous Novel Primate- and Tissue-Specific microRNAs," *PNAS*, 112: e1106-1115, 2015.
Miyaki, et al., "MicroRNA-140 is Expressed in Differentiated Human Articular Chondrocytes and Modulates Interleukin-1 Responses," *Arthritis & Rheumatology*, 60: 2723-2730, 2009.
Miyaki, et al., "MicroRNA-140 Plays Dual Roles in Both Cartilage Development and Homeostasis," *Genes & Development*, 24: 1173-1185, 2010.
Nakamura, et al., "Identification of microRNA-181a-5p and microRNA-4454 as Mediators of Facet Cartilage Degeneration," *JCI Insight*, 1(12): e86820, 2016.
Pfirrman, et al., "Magnetic Resonance Classification of Lumbar Intervertebral Disc Degeneration," *Spine*, 26: 1873-1878, 2001.
Pritzker, et al., "Osteoarthritis Cartilage Histopathology: Grading and Staging," *Osteoarthritis & Cartilage*, 14: 13-29, 2006.
Sasaki, et al., "Phosphorylation of RelA/p65 on Serine 536 Defines an IκBα-Independent NF-κβPathway," *Journal of Biological Chemistry*, 280: 34538-34547, 2005.
Shirdel, et al., "NAVIGaTing the Micronome—Using Multiple MicroRNA Prediction Databases to Identify Signalling Pathway-Associated microRNAs," *PloS One*, 6: e17429, 2011.
Song, et al., "MicroRNA-181b Regulates Articular Chondrocytes Differentiation and Cartilage Integrity," *Biochemical and Biophysical Research Communications*, 431(2): 210-214, 2013.
Sumiyoshi, et al., "Novel Role of miR-181a in Cartilage Metabolism," *J Cell Biochem*, 114: 2094-2100, 2013.
Sun, et al., "MicroRNA-34a Suppresses Cell Proliferation and Induces Apoptosis in U87 Glioma Stem Cells," *Technology in Cancer Research Treatment*, 11(5): 483-490, 2012.
Suri, et al., "Presence and Extent of Severe Facet Joint Arthritis are Associated with Back Pain in Older Adults," *Osteoarthritis Cartilage*, 21: 1199-1206, 2013.
Tardif, et al., "NFAT3 and TGF-β/SMAD3 Regulate the Expression of miR-140 in Osteoarthritis," *Arthritis Research & Therapy*, 15: R197, 2013.
Tardif, et al., "Regulation of the IGFBP-5 and MMP-13 Genes by the microRNAs miR-140 and miR-27a in Human Osteoarthritic Chondrocytes," *BMC Musculoskeletal Disorders*, 10: 148, 2009.
Tuddenham, et al., "The Cartilage Specific microRNA-140 Targets Histone Deacetylase 4 in Mouse Cells," *FEBS Letters*, 580: 4214-4217, 2006.
Voinnet, "Origin, Biogenesis, and Activity of Plant microRNAs," *Cell*, 136: 669-687, 2009.
Weishaupt, "MR Imaging and CT in Osteoarthritis of the Lumbar Facet Joints," *Skeletal Radiology*, 28: 215-219, 1999.
Yamasaki, et al., "Expression of microRNA146a in Osteoarthritis Cartilage," *Arthritis Rheumatology*, 60: 1035-1041, 2009.
Zhang, et al., "Cartilage-Specific Deletion of mTOR Upregulates Autophagy and Protects Mice from Osteoarthritis," *Annals Rheumatic Diseases*, 74: 1432-1440, 2015.
Zhou, et al., "NF-κβ Target microRNAs and Their Target Genes in TNFα-Stimulated HeLA Cells," *Biochimica et Biophysica Acta (BBA)—Gene Regulatory Mechanisms*, 1839(4): 344-354, 2014.

* cited by examiner

Fig. 1A and 1B
A.
MRI Grading Scale
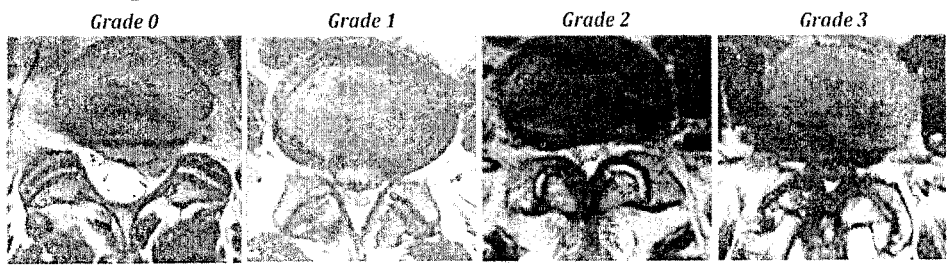
Grade 0  Grade 1  Grade 2  Grade 3
Safranin O/Fast Green staining
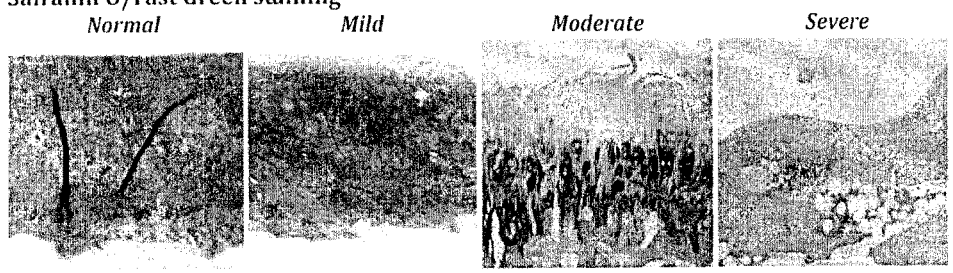
Normal  Mild  Moderate  Severe
B. OARSI score
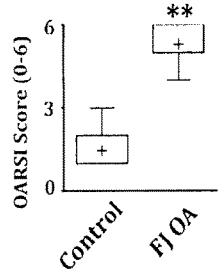

Fig. 1 C and 1D
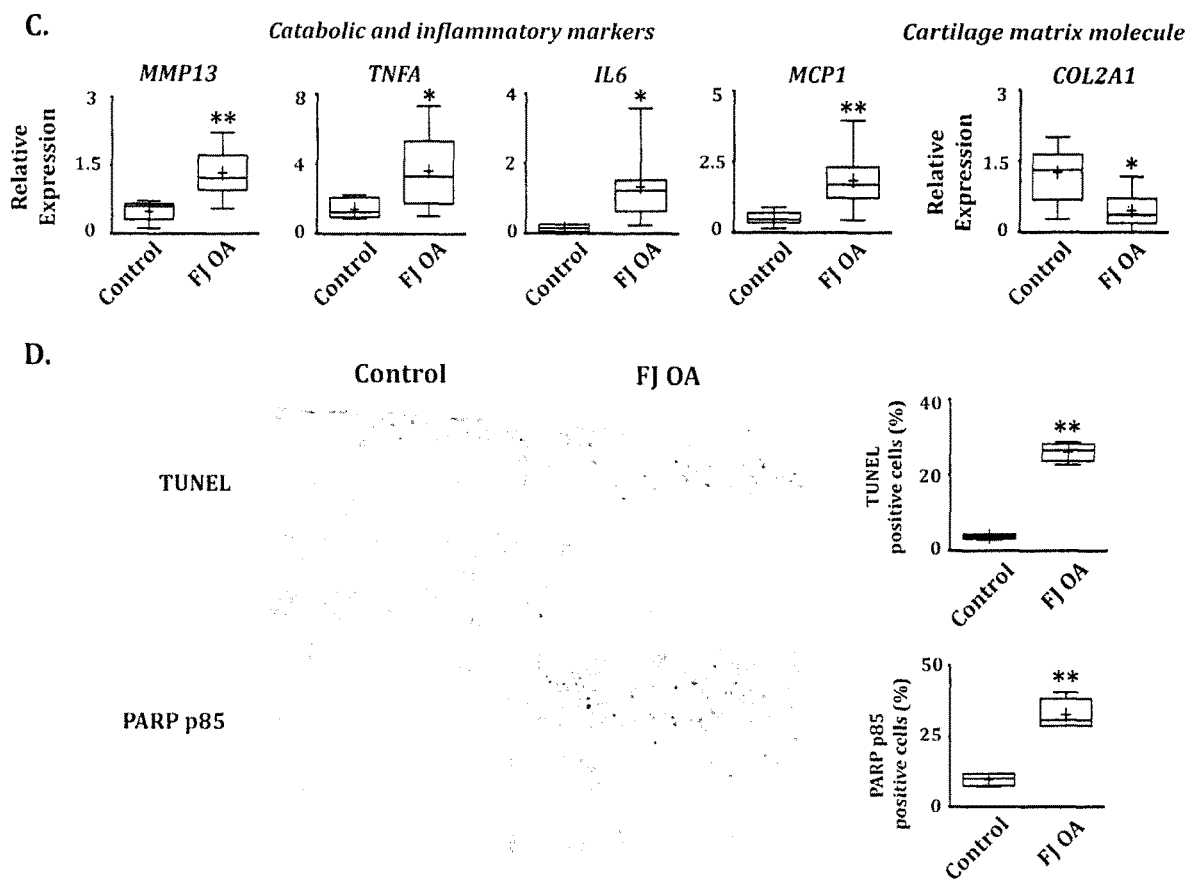

Fig. 2 A and 2B
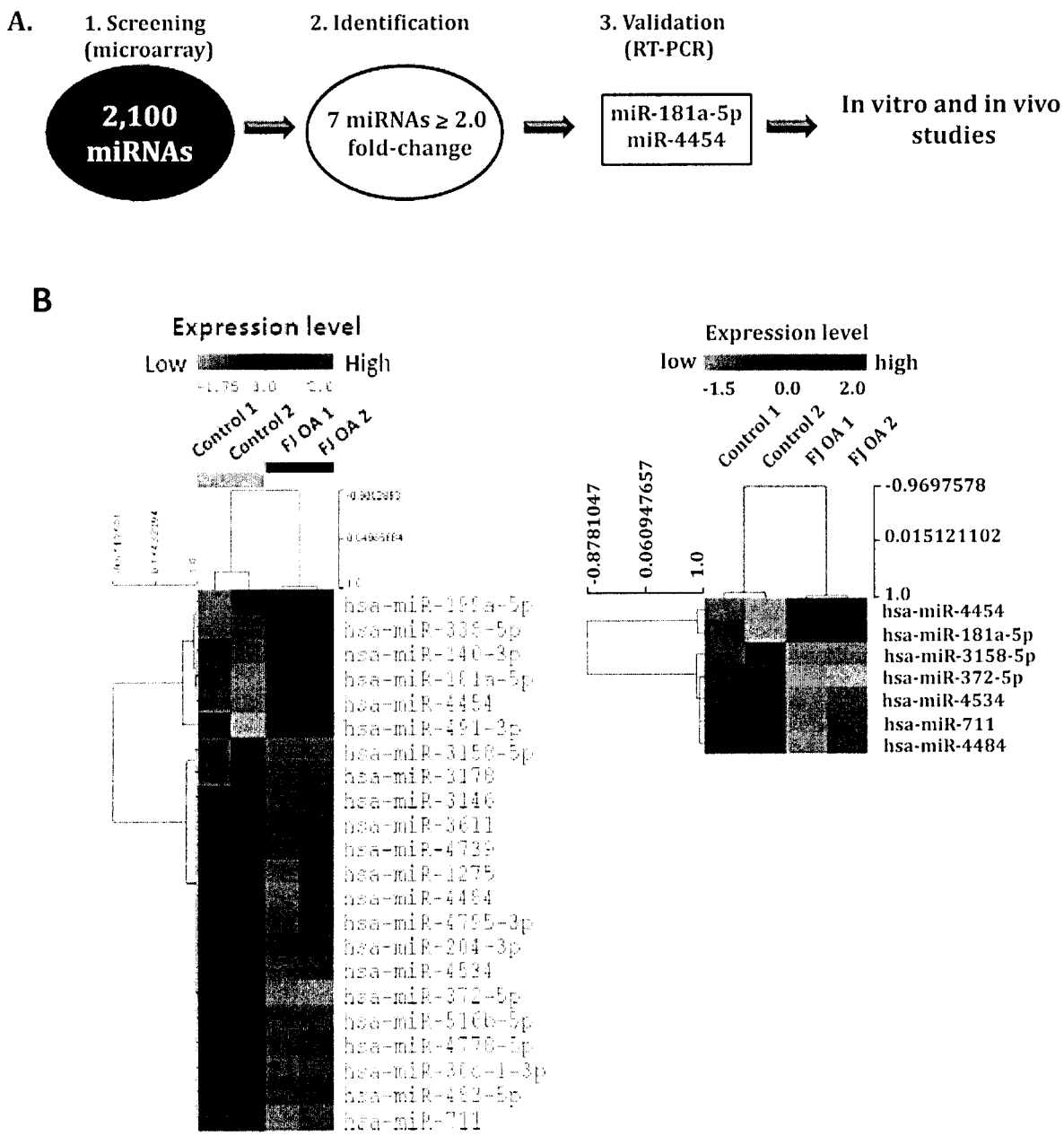

Fig. 2 C and 2D
C.
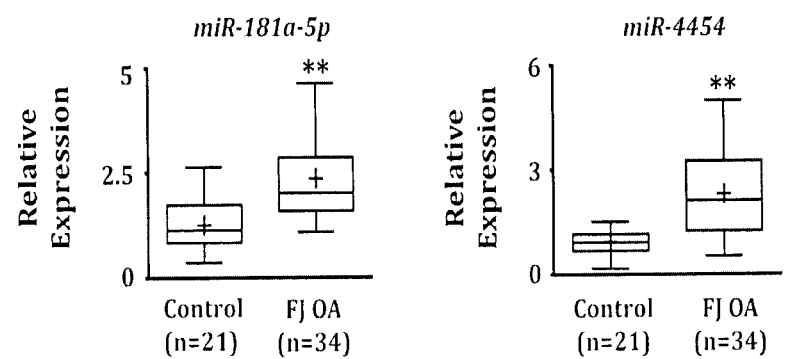
D.
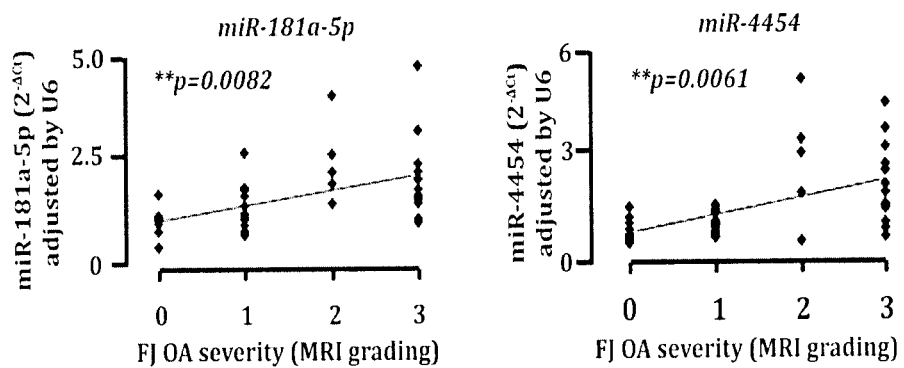

C.

Fig. 4A, 4B, and 4C
A. Potential target genes for miR-181a-5p and miR-4454
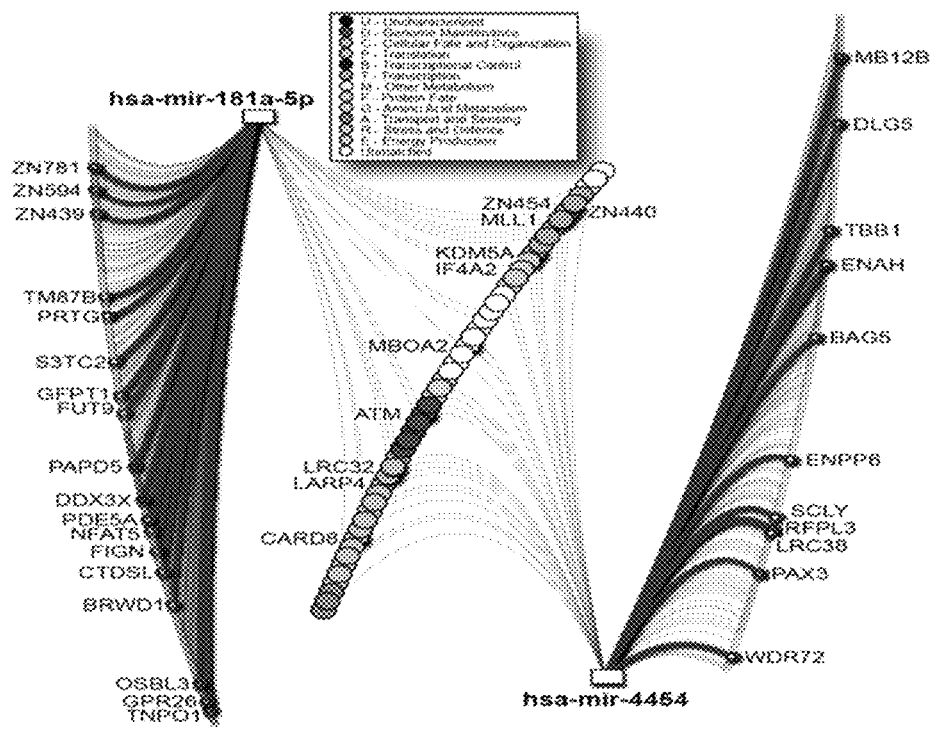
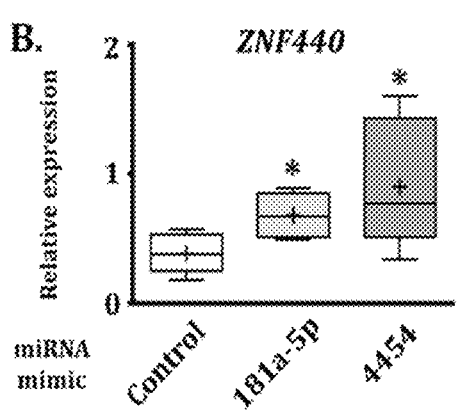
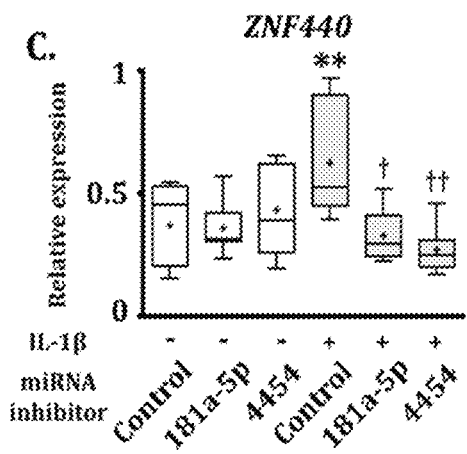

Fig. 4D, 4E, and 4F
D. Enriched target pathways for miR-181a-5p and miR-4454
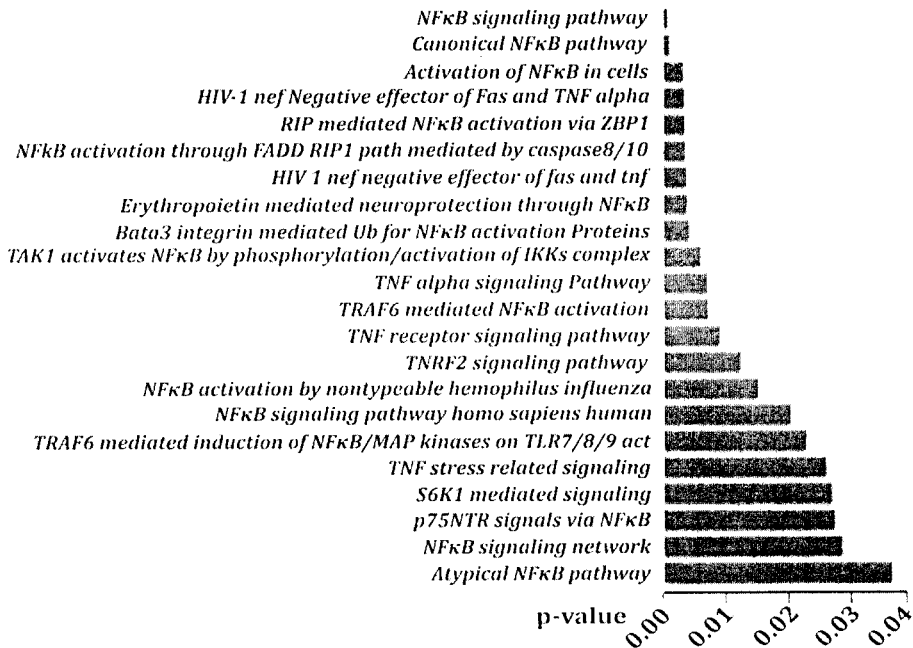
E.
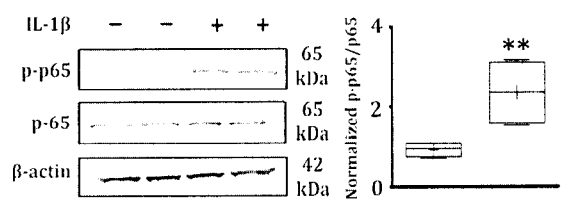
F.
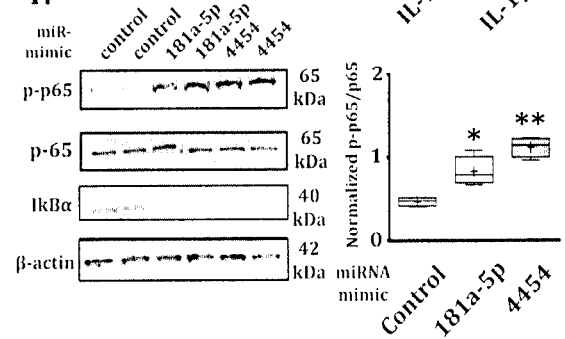

SEQUENCE LISTING

<160> NUMBER OF SEQ ID NOS: 45

<210> SEQ ID NO 1
<211> LENGTH: 23
<212> TYPE: RNA
<213> ORGANISM: Homo sapiens

<400> SEQUENCE: 1
aacauucaac gcugucggug agu                                              23

<210> SEQ ID NO 2
<211> LENGTH: 20
<212> TYPE: RNA
<213> ORGANISM: Homo sapiens

<400> SEQUENCE: 2
ggauccgagu cacggcacca                                                  20

<210> SEQ ID NO 3
<211> LENGTH: 21
<212> TYPE: DNA
<213> ORGANISM: Artificial Sequence
<220> FEATURE:
<223> OTHER INFORMATION: LNA inhibitor
<220> FEATURE:
<221> NAME/KEY: misc_feature
<222> LOCATION: (1)..(21)
<223> OTHER INFORMATION: LNA

<400> SEQUENCE: 3
actcaccgac agcgttgaat g                                                21

<210> SEQ ID NO 4
<211> LENGTH: 19
<212> TYPE: DNA
<213> ORGANISM: Artificial Sequence
<220> FEATURE:
<223> OTHER INFORMATION: LNA inhibitor
<220> FEATURE:
<221> NAME/KEY: misc_feature
<222> LOCATION: (1)..(19)
<223> OTHER INFORMATION: LNA

<400> SEQUENCE: 4
tggtgccgtg actcggatc                                                   19

<210> SEQ ID NO 5
<211> LENGTH: 22
<212> TYPE: DNA
<213> ORGANISM: Homo sapiens

<400> SEQUENCE: 5
tcaccgggtg taaatcagct tg                                               22

<210> SEQ ID NO 6
<211> LENGTH: 19
<212> TYPE: DNA
<213> ORGANISM: Artificial Sequence
<220> FEATURE:
<223> OTHER INFORMATION: Negative Control A

<400> SEQUENCE: 6
taacacgtct atacgccca                                                   19

<210> SEQ ID NO 7
<211> LENGTH: 21

```
<212> TYPE: DNA
<213> ORGANISM: Artificial Sequence
<220> FEATURE:
<223> OTHER INFORMATION: Primer

<400> SEQUENCE: 7
cagaacatca tccctgcctc t                                          21

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
tcccaggaat tggtgataag taga                                       24

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
tggacgatca cgaaacc                                               17

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
gtctcctacc agaccaag                                              18

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
tgacaaacaa attcggtaca tcct                                       24

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
ctctgccgcc cttctgtg                                              18

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
```

```
catcatgccc agctgcaacc                                           20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgcctccata gcactttgcc                                           20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
actgtggcgc caagaaatgc                                           20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgtgcaaaag ggggagaagg                                           20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gagccacttg tcatgcctgc                                           20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tgaaacaagc acccatgc                                             18

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ccagcaaatt ctagtgccag tcag                                      24

<210> SEQ ID NO 20
<211> LENGTH: 20
<212> TYPE: DNA
<213> ORGANISM: Artificial Sequence
```

<220> FEATURE:
<223> OTHER INFORMATION: Primer

<400> SEQUENCE: 20
tcaagcggct caatcttgcc                                          20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agacccggaa gcagttgttg                                          20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gatggagtcg taggggcctg ag                                       22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gcttgacaaa gtggtcgttg ag                                       22

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ctggcatgac gcgaacaa                                            18

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gctgcggatg ctctcaatct                                          20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
caaagtagac ctgcccagac tc                                       22

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tctgccagtg cctctttgct                                                    20

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
tgcatctggc tgagcgag                                                      18

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atggcactgc tggtcttggg                                                    20

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gccttcatcc ttgaaggtca cc                                                 22

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tcagcgttgc tttggatggc                                                    20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
aacacttgac ggcacacctg                                                    20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
acacgacttg accctgaccg                                                   20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
acggacaagt gctgaggttg                                                   20

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
tgaggtggat taggagcagg atc                                               23

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ttgtttcgca ggtccagcac                                                   20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
aaggacacac actcgccttg                                                   20

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ctccctcatc agggcttca cg                                                 22

<210> SEQ ID NO 39
<211> LENGTH: 23
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(23)
<223> OTHER INFORMATION: LNA

<400> SEQUENCE: 39
ccucaaaugu ggagcacuau ucu                                              23

<210> SEQ ID NO 40
<211> LENGTH: 21
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(21)
<223> OTHER INFORMATION: LNA

<400> SEQUENCE: 40
ccugcagaga ggaagcccuu c                                                21

<210> SEQ ID NO 41
<211> LENGTH: 22
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(22)
<223> OTHER INFORMATION: LNA

<400> SEQUENCE: 41
gggacccagg gagagacgua ag                                               22

<210> SEQ ID NO 42
<211> LENGTH: 20
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: LNA

<400> SEQUENCE: 42
ggauccgagu cacggcacca                                                  20

<210> SEQ ID NO 43
<211> LENGTH: 17
<212> TYPE: RNA
<213> ORGANISM: Artificial Sequence
<220> FEATURE:
<223> OTHER INFORMATION: primer

<400> SEQUENCE: 43
ggauggagga ggggucu                                                     17

<210> SEQ ID NO 44
<211> LENGTH: 23
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(23)
<223> OTHER INFORMATION: LNA

<400> SEQUENCE: 44
aacauucaac gcugucggug agu                                              23

```
<210> SEQ ID NO 45
<211> LENGTH: 20
<212> TYPE: RNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: LNA

<400> SEQUENCE: 45
aaaaggcggg agaagcccca                                              20
```

MIRNA BIOMARKERS FOR CARTILAGE DEGENERATION

CROSS-REFERENCE TO RELATED APPLICATIONS

This application is a national phase application under 35 U.S.C. § 371 of International Application No. PCT/CA2017/000019 filed Jan. 31, 2017, which claims the benefit of U.S. Provisional Patent Application Ser. No. 62/299,305 filed Feb. 24, 2016, the entire contents of which are hereby incorporated by reference.

FIELD OF THE INVENTION

This invention relates generally to cartilage degeneration, and more particularly to methods, inhibitors, uses and systems for detecting, diagnosing, prognosing, treating or preventing cartilage degeneration.

BACKGROUND OF THE INVENTION

The degeneration of facet cartilage is a hallmark of facet joint osteoarthritis (FJ OA). Radiographically, FJ OA appears similar to that seen in appendicular synovial joints (see FIGS. 7A and 7B); however, the specific mechanisms associated with facet cartilage degeneration during FJ OA are largely unknown. Due to the lack of biomarkers, it is impossible to identify patients exhibiting early stages of FJ OA, leading to severe cartilage degeneration and associated low back pain with or without leg symptoms[1]. Furthermore, due to poor understanding of the underlying mechanisms associated with degeneration of facet cartilage, no targeted therapies to treat FJ OA exist. In order to devise appropriate therapeutic strategies to stop or delay facet cartilage degeneration, it is critical to first dissect endogenous mechanisms associated with facet cartilage degeneration.

MicroRNAs (miRNAs) are small non-coding RNAs that are expressed as primary stem loop precursors and undergo maturation by enzymatic processes[2-4]. The mature forms are single-stranded non-coding RNA molecules of 20-23 nucleotide length that usually bind to the 3' untranslated region (UTR) of the target mRNAs and destabilize them or inhibit their translation[5]. There are more than 3,700 annotated miRNAs from the human genome and this number is increasing[6]. It is estimated that miRNAs regulate over 60% of all coding genes and play pivotal roles in physiological processes including cell proliferation, differentiation, genomic stability, metabolism, apoptosis and aging.[7-9]

The role of miRNAs in facet cartilage degeneration has never been reported. However, recent studies performed in knee or hip OA do suggest a pathophysiological role for miRNAs during OA pathogenesis. MiR-140 is the most widely investigated miRNA in knee OA research. It was first reported as a cartilage-specific miRNA in mice that directly targeted histone deacetylase 4 (HDAC4)[10]. MiR-140 has been shown to regulate cartilage development and homeostasis, and its loss contributes to the development of age-related knee OA-like phenotype (miyaki et al). In human knee cartilage, miR-140 is up-regulated during chondrogenesis, whereas it is down-regulated in human knee OA chondrocytes[2, 11-13]. Further, it has been identified that human knee chondrocytes treated by interleukin (IL)-1β resulted in the suppression in the expression of miR-140 accompanied by enhanced expression of catabolic markers (matrix metalloproteinase [MMP-13], a disintegrin-like and metalloproteinase with thrombospondin type 1 motifs-5 [ADAMTS5]) and decreased expression of aggrecan[2, 11-13]. MiR-146 has been shown to be highly expressed in low-grade OA cartilage and is induced by IL-1β stimulation and mediates chondrocyte apoptosis[14, 15]. In serum, Beyer et al. recently reported miRNA let-7e as a potential predictor for severe knee or hip OA[16].

Therefore, there is a need for an improved diagnosis, estimate of prognosis, and treatment for cartilage degeneration.

SUMMARY OF THE INVENTION

In an embodiment of the present disclosure, there is provided a method of treating or preventing a disease or condition comprising cartilage degeneration, preferably facet cartilage degeneration, in a subject in need thereof, the method comprising inhibiting at least one of miR-181a-5p and miR-4454, in the subject.

In another embodiment of the present disclosure, there is disclosed an antisense oligonucleotide for use in the treatment or prevention of a disease or condition comprising joint degeneration in a subject in need thereof, wherein the antisense oligonucleotide inhibits at least one of miR-181a-5p and miR-4454.

In yet another embodiment of the present disclosure, there is disclosed a use of an antisense oligonucleotide in the preparation of a medicament for the treatment or prevention of a disease or condition comprising joint degeneration in a subject in need thereof, wherein the antisense oligonucleotide inhibits at least one of miR-181a-5p and miR-4454.

In another embodiment of the present disclosure, there is disclosed an antisense oligonucleotide that inhibits at least one of miR-181a-5p and miR-4454, with the proviso that the antisense oligonucleotide is not SEQ ID NO. 3 or SEQ ID NO. 4.

In another embodiment of the present disclosure, there is disclosed a method for the diagnosis or prognosis of cartilage degeneration in a patient comprising: (a) obtaining a sample from the patient; (b) generating a sample RNA expression profile for at least one of miR-181a-5p and miR-4454; (c) comparing the sample RNA expression profile to at least one of a degenerated cartilage reference profile and non-degenerated cartilage reference profile; wherein a statistically significant upregulation of at least one of miR-181a-5p and miR-4454 is indicative of cartilage degeneration.

In another embodiment of the present disclosure, there is described a method, performed by at least one computing device, for the diagnosis or prognosis of cartilage degeneration in a patient: (a) determining, at the processor, a sample RNA expression profile from RNA expression input for at least one of SEQ ID No. 1 and SEQ ID. NO. 2 based on a sample from the patient; (b) determining, by the processor, the statistical distance between the sample RNA expression profile and at least one of a degenerated cartilage reference profile and non-degenerated cartilage reference profile stored in a computer readable storage medium; wherein the statistical distance between the sample RNA expression profile and at least one of the degenerated cartilage reference profile and non-degenerated cartilage reference profile is associated with cartilage degeneration in the patient; (c) displaying a diagnosis or prognosis of cartilage degeneration if the statistical distance is greater than a predetermined threshold statistical distance.

In yet another embodiment of the present disclosure, there is disclosed a system for the diagnosis or prognosis of cartilage degeneration in a patient: a non-transitory computer readable storage medium that stores computer-readable code; a processor operatively coupled to the non-transitory computer readable storage medium, the processor configured to implement the computer-readable code, the computer-readable code configured to: generate a sample RNA expression profile from RNA expression input for at least one of SEQ ID No. 1 and SEQ ID. NO. 2 based on a sample from the patient; compare the sample RNA expression profile to at least one of a degenerated cartilage reference profile and non-degenerated cartilage reference profile stored in a same or different non-transitory computer readable storage medium; calculate the statistical distance between the sample RNA expression profile and at least one of the degenerated cartilage reference profile and non-degenerated cartilage reference profile; wherein the statistical distance between the sample RNA expression profile and at least one of the degenerated cartilage reference profile and non-degenerated cartilage reference profile is associated with cartilage degeneration in the patient; and outputting a diagnosis of cartilage degeneration if the statistical distance is greater than a predetermined threshold statistical distance.

Accordingly, in an aspect, there is provided a method for the prognosis of cartilage degeneration, preferably facet cartilage degeneration, in a patient comprising: (a) obtaining a sample of the patient; (b) generating a sample RNA expression profile for at least one of miR-181a-5p and miR-4454; (c) comparing the sample RNA expression profile to at least one of a degenerated facet cartilage reference profile and non-degenerated facet cartilage reference profile; wherein the degree of statistically significant upregulation of at least one of miR-181a-5p and miR-4454 is correlative with the severity of the facet cartilage degeneration.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

Embodiments will now be described, by way of example only, with reference to the attached figures, wherein:

FIG. 1 shows (A) MRI image and histological analyses of facet joint degeneration. Representative magnetic resonance imaging (MRI) of patients with lumbar disc herniation (LDH; n=21) showing Grade 0 (normal) or Grade 1 (mild) FJ degeneration score and facet joint osteoarthritis (FJ OA; n=34) patients showing Grade 2 (moderate) or Grade 3 (severe) FJ degeneration exhibiting narrowed joint space and presence of osteophytes. Histological analysis using Safranin O/fast green staining showing facet cartilage with no degeneration, mild degeneration, moderate degeneration and severe degeneration. Original magnification: 10×. (B) Osteoarthritis Research Society International (OARSI) scores in control (n=21) and FJ OA (n=34) cartilage. (C) Expression of OA catabolic, inflammatory and matrix markers: Real-time PCR (RT-PCR) showed significant increase in the expression of major catabolic marker (MMP13), inflammatory markers (TNFA, IL6, MCP1) and decrease in the expression of major cartilage matrix molecule (COL2A1) in FJ OA cartilage (n=12) compared to control cartilage (n=7). (D) Representative immunohistochemistry images of control (grade 0) and FJ OA cartilage (grade 3) stained for Poly (ADP-ribose) polymerase (PARP) p85 and TUNEL. Number of PARP p85 and TUNEL positive cells in FJ OA cartilage compared to control cartilage were quantified (n=4/group). Original magnification: 20×. (A-D) All data presented as box-and-whiskers plots. Horizontal lines and cross marks indicate the medians and the means, boxes indicate 25th to 75th percentiles, and whiskers indicate minimum and maximum values of the dataset. The significance of differences in the levels of expression between the control and FJ OA groups was determined using a two-tailed Student's T test. *, $p<0.05$, **, $p<0.01$.

FIG. 2 shows screening, identification and validation of miRNAs. (A) Schematic flow chart showing screening, identification, and validation of miRNAs in FJ OA cartilage compared to control LDH cartilage. (B) A panel of differentially expressed 22 miRNAs ($\geq 1.5$-fold change) and 7 miRNAs ($\geq 2.0$-fold change) between FJ OA and control LDH cartilage. List of miRNAs with $\geq 2.0$-fold change in FJ OA compared to control LDH facet cartilage was further validated by RT-PCR. (C) Significant increase in the expression of miR-181a-5p and miR-4454 in FJ OA (n=34) compared to control (n=21) by RT-PCR. *$p<0.05$, $p<0.01$. (D) Correlation between the expression of miR-181a-5p or miR-4454 and severity of FJ OA based on MRI grading. Ordinal logistic regression model showing a significant positive correlation between the expression of miR-181a-5p (p=0.0082) or miR-4454 (p=0.0061) and MRI grading score (Total=55 patients: 21 from control group and 34 from FJ OA group). , $p<0.01$.

DETAILED DESCRIPTION

Figures 3A, 3B:
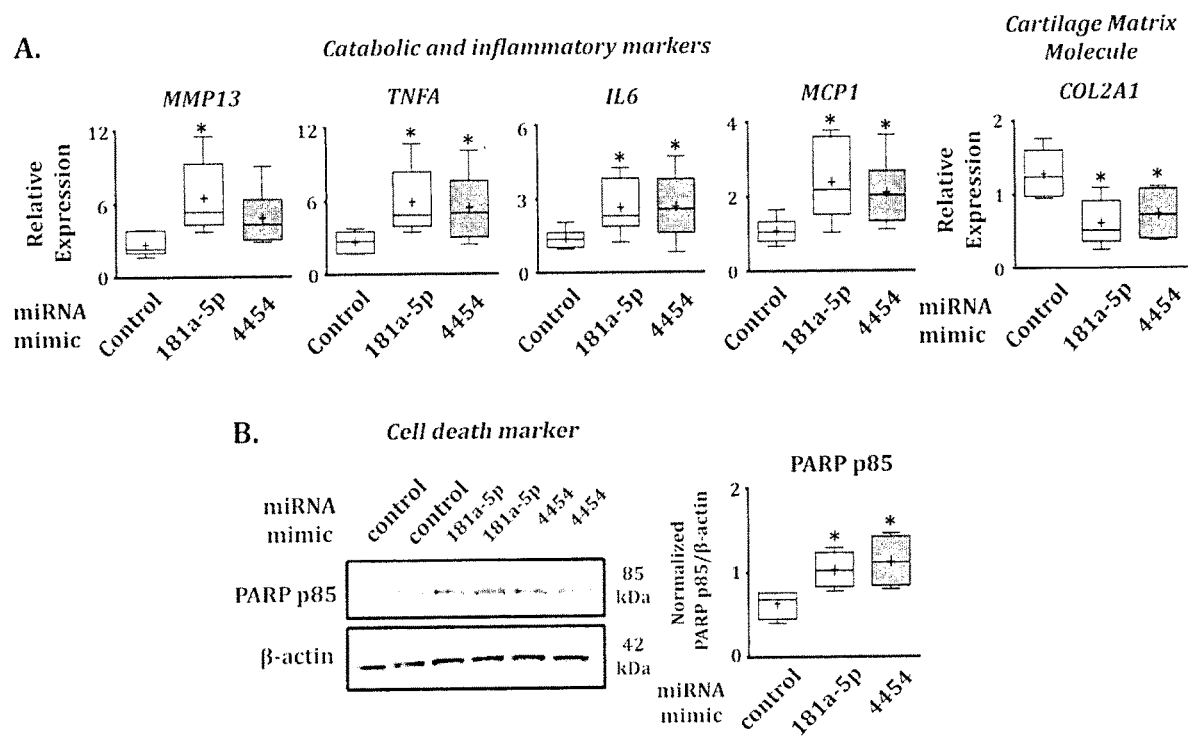
FIG. 3 shows effect of miR-181a-5p and miR-4454 mimic or inhibitors on the expression of catabolic, inflammatory, cell death and matrix markers in facet joint osteoarthritis (FJ OA) chondrocytes. (A) Real-time PCR (RT-PCR) analysis of the expression of major cartilage catabolic (MMP13) and inflammatory (TNFA, IL6 and MCP1) markers, and the cartilage matrix molecule COL2A1 in FJ OA chondrocytes treated with miR-181a-5p or miR-4454 mimic compared to control mimic (n=6/treatment). (B) PARP p85 expression relative to β-actin expression by Western blotting in FJ OA chondrocytes treated with miR-181a-5p or miR-4454 mimic compared to control mimic. Representative blot from n=4 separate blots. (A&B) *, $p<0.05$ between control and miR-181a-5p or miR-4454 mimics by two-tailed Student's T-test. (C) RT-PCR analysis of miR-181a-5p and miR-4454 in FJ OA chondrocytes treated with (+) or without (−) IL-1β (n=7/treatment). *, $p<0.05$, **, $p<0.01$ as determined by a two-tailed Student's T-test. (D) RT-PCR analysis of catabolic, inflammatory and cell death markers and COL2A1 in FJ chondrocytes treated with (+) or without (−) IL-1β and miR-181a-5p, miR-4454, or control inhibitors (n=7/treatment). (E) Immunoblot analysis of PARP p85 protein levels relative to β-actin in FJ OA chondrocytes treated with miR-181a-5p and miR-4454 inhibitors compared to control inhibitor in the presence (+) or absence (−) of IL-1β. Representative blot from n=4 separate blots. (D&E) Differences in the levels of expression between miR-181a-5p, miR-4454 and control inhibitor, with (+) or without (−) IL-1β treatment was determined one-way analysis of variance followed by Tukey's post-hoc tests.*, $p<0.05$, **, $p<0.01$, control inhibitor without IL-1l3 treatment vs. control inhibitor with IL-1β treatment. †, $p<0.05$ or ††, $p<0.01$, control inhibitor treatment vs miR-181a-5p or miR-4454 inhibitor treatment in the presence of IL-1β, respectively. All other comparisons were not significantly different (p>0.05). All data presented as box-and-whiskers plots. Horizontal lines and cross marks indicate the medians and the means, boxes indicate 25th to 75th percentiles, and whiskers indicate minimum and maximum values of the dataset.

Embodiments of methods, uses, systems, and apparatus suitable for use in implementing the invention are described through reference to the drawings.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In an aspect of the present disclosure, there is provided a method of treating or preventing a disease or condition comprising cartilage degeneration, preferably facet cartilage degeneration, in a subject in need thereof, the method comprising inhibiting at least one of miR-181a-5p and miR-4454, in the subject.

In an aspect, miR-181a-5p and miR-4454 are represented by SEQ ID NOs. 1 and 2.

In some aspects of the present disclosure, inhibiting comprises administering to the subject a therapeutically effective amount of an inhibitor of at least one of miR-181a-5p and miR-4454, preferably directly injected at the site of the facet cartilage degeneration.

As used herein, "therapeutically effective amount" refers to an amount effective, at dosages and for periods of time necessary, to achieve the desired therapeutic result. A therapeutically effective amount of inhibitor may vary according to factors such as the disease state, age, sex, and weight of the individual, and the ability of the inhibitor to elicit a desired response in the individual. A therapeutically effective amount is also one in which any toxic or detrimental effects of the inhibitor are outweighed by the therapeutically beneficial effects.

In an aspect, the method comprises inhibiting both of miR-181a-5p and miR-4454.

In some aspects, the inhibitor is an antisense oligonucleotide having a nucleotide sequence that is complementary to at least 80%, 90%, 95%, 98%, 99% or 100% of SEQ ID NO: 1 or SEQ ID NO. 2.

As used herein, the term "complementary" refers to the concept of sequence complementarity between regions of two nucleotide strands. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 80%, 90%, 95%, 98%, 99% or 100% complementary) that contains mismatched nucleotides at one or more nucleotide positions. In one embodiment, two complementary polynucleotides are capable of hybridizing to each other under certain hybridization conditions, as defined herein.

In other aspects, the inhibitor is an antisense oligonucleotide having a nucleotide sequence comprising SEQ ID NO: 3 or SEQ ID NO. 4, or a functional fragment thereof.

The term "oligonucleotide" as used herein refers to a nucleic acid molecule from about 2 to about 100 nucleotides, preferably 5-50, 5-30, or 10-20 nucleotides.

In an aspect, the antisense oligonucleotide consists of SEQ ID NO. 3 or SEQ ID NO. 4.

In some aspects, the antisense oligonucleotides is two antisense oligonucleotides consisting of SEQ ID NO. 3 and SEQ ID NO. 4.

In yet other aspects of the present disclosure, the inhibitor is an antisense oligonucleotide having at least 80%, 90%, 95%, 98% or 99% sequence identity to any one of SEQ ID NO: 3 or SEQ ID NO: 4, or a functional fragment thereof.

In other aspects, the inhibitor is an antisense oligonucleotide capable of hybridizing under stringent conditions, preferably highly stringent conditions, to a nucleotide sequence of any one of SEQ ID NO: 1 and SEQ ID NO: 2.

As used herein, "stringent conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. Post-hybridization washes may also determine stringency conditions. For selective or specific hybridization, a positive signal can be at least 2 to 10 times background hybridization. One set of stringent conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min.

As used herein, "highly stringent conditions" involves the use of higher temperatures in which the washes are identical to those defined above, except the temperature of the final two 30 min. washes in 0.2×SSC, 0.5% SDS is increased to 60° C. Another example of highly stringent conditions involves the use of two final washes in 0.1×SSC, 0.1% SDS at 65° C. In yet another example of highly stringent conditions, the conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

In some aspects of the present disclosure, the disease or condition is facet joint osteoarthritis or physical trauma to cartilage, preferably related to spinal canal stenosis.

In another embodiment of the present disclosure, there is disclosed an antisense oligonucleotide for use in the treatment or prevention of a disease or condition comprising joint degeneration or cartilage degeneration in a subject in need thereof, wherein the antisense oligonucleotide inhibits at least one of miR-181a-5p and miR-4454.

In some embodiments, the antisense oligonucleotide has a nucleotide sequence that is complementary to at least 80%, 90%, 95%, 98%, 99% or 100% of SEQ ID NO: 1 or SEQ ID NO. 2.

In other aspects, the antisense oligonucleotide has a nucleotide sequence comprising SEQ ID NO: 3 or SEQ ID NO. 4, or a functional fragment thereof.

In yet other aspects, the antisense oligonucleotide consists of SEQ ID NO. 3 or SEQ ID NO. 4.

In further aspects, the antisense oligonucleotide is two antisense oligonucleotides consisting of SEQ ID NO. 3 and SEQ ID NO. 4.

In yet additional aspects, the antisense oligonucleotide has at least 80%, 90%, 95%, 98% or 99% sequence identity to any one of SEQ ID NO: 3 or SEQ ID NO: 4, or a functional fragment thereof.

In yet other aspects, the antisense oligonucleotide is capable of hybridizing under stringent conditions, preferably highly stringent conditions, to a nucleotide sequence of any one of SEQ ID NO: 1 and SEQ ID NO: 2.

In some aspects, the disease or condition is facet joint osteoarthritis or physical trauma to cartilage, preferably related to spinal canal stenosis.

In another embodiment of the present disclosure, there is disclosed a use of an antisense oligonucleotide in the treatment or prevention of a disease or condition comprising joint degeneration in a subject in need thereof, wherein the antisense oligonucleotide inhibits at least one of miR-181a-5p and miR-4454.

In yet another embodiment of the present disclosure, there is disclosed a use of an antisense oligonucleotide in the preparation of a medicament for the treatment or prevention of a disease or condition comprising joint degeneration in a subject in need thereof, wherein the antisense oligonucleotide inhibits at least one of miR-181a-5p and miR-4454.

In another embodiment of the present disclosure, there is disclosed an antisense oligonucleotide that inhibits at least one of miR-181a-5p and miR-4454, with the proviso that the antisense oligonucleotide is not SEQ ID NO. 3 or SEQ ID NO. 4.

In an aspect, the antisense oligonucleotide has a nucleotide sequence that is complementary to at least 80%, 90%, 95%, 98%, 99% or 100% of SEQ ID NO: 1 or SEQ ID NO. 2.

In yet another aspect, the antisense oligonucleotide has at least 80%, 90%, 95%, 98% or 99% sequence identity to any one of SEQ ID NO: 3 or SEQ ID NO: 4, or a functional fragment thereof.

In yet another aspect, the antisense oligonucleotide is capable of hybridizing under stringent conditions, preferably highly stringent conditions, to a nucleotide sequence of any one of SEQ ID NO: 1 and SEQ ID NO: 2.

In another embodiment of the present disclosure, there is disclosed a method for the diagnosis of cartilage degeneration, preferably facet cartilage degeneration, in a patient comprising: (a) obtaining a facet cartilage sample of the patient; (b) generating a sample RNA expression profile for at least one of miR-181a-5p and miR-4454; (c) comparing the sample RNA expression profile to at least one of a degenerated facet cartilage reference profile and non-degenerated facet cartilage reference profile; wherein a statistically significant up-regulation of at least one of miR-181a-5p and miR-4454 is indicative of facet cartilage degeneration.

As used herein, "diagnosis" refers to the process of determining whether cartilage degeneration is present in a subject. Diagnosis may include the determination of the severity of cartilage degeneration.

In some aspects, the method is directed to estimating prognosis for cartilage degeneration, preferably facet cartilage degeneration, correlating the up-regulation of at least one of miR-181a-5p and miR-4454 with symptoms, or estimating response to a given local or system treatment.

Accordingly, in an aspect, there is provided a method for the prognosis of cartilage degeneration, preferably facet cartilage degeneration, in a patient comprising: (a) obtaining a sample of the patient; (b) generating a sample RNA expression profile for at least one of miR-181a-5p and miR-4454; (c) comparing the sample RNA expression profile to at least one of a degenerated facet cartilage reference profile and non-degenerated facet cartilage reference profile; wherein the degree of statistically significant upregulation of at least one of miR-181a-5p and miR-4454 is correlative with the severity of the facet cartilage degeneration.

The term "prognosing or classifying" as used herein means predicting or identifying a clinical outcome for a subject according to the subject's similarity to a reference profile or biomarker expression level associated with the prognosis. For example, prognosing or classifying may comprise determining whether an individual with cartilage degeneration will likely have a good or poor outcome, or grouping an individual with cartilage degeneration into a good outcome group or a poor outcome group. Prognosis may also refer to the determination of whether or not an individual with cartilage degeneration will respond to therapy or is responding to therapy.

In an embodiment, the prognosis of cartilage degeneration is in a patient receiving treatment, wherein the degenerated cartilage reference profile is a previous RNA expression profile from the same patient and a decrease in miR-181a-5p and/or miR-4454 expression is indicative of a positive response to treatment, and an increase or no change in miR-181a-5p and/or miR-4454 expression levels is indicative of a negative or nul response to treatment.

In some aspects, the method further comprises (d) calculating the statistical distance between the sample RNA expression profile and at least one of the degenerated facet cartilage reference profile and non-degenerated facet cartilage reference profile; wherein the statistical distance between the sample RNA expression profile and at least one of the degenerated facet cartilage reference profile and non-degenerated facet cartilage reference profile is associated with facet cartilage degeneration in the patient.

In yet other aspects, the method further comprises treating the patient with one or more of the methods recited herein.

In an aspect, there is described a method for identifying or evaluating therapies for cartilage degeneration utilizing the finding that miR-181a-5p and/or miR-4454 are significantly elevated in degenerated cartilage and exhibit a positive correlation with disease severity. In an embodiment of the present disclosure, there is described a method of identifying or evaluating therapies for cartilage degeneration, the method comprising providing an animal with increased miR-181a-5p and/or miR-4454. The increased miR-181a-5p and/or miR-4454 may be achieved by locally injecting miR-181a-5p and/or miR-4454 into an animal, transgenic manipulations or other known physical or genetic means. The animal may then be used to screen potential candidates, or evaluate potential therapies, by subjecting the animal to the candidates or therapies and evaluating the therapeutic or preventative effects thereof on cartilage degeneration.

The animal model is preferably a non-human mammal. For example, the animal model may be a rodent or non-human primate. In some embodiments, the animal is selected from the group consisting of a mouse, rat, guinea pig, hamster, gerbil, pig, cow, dog, wolf, coyote, jackel, and cat. In some embodiments, the animal model is a monkey or ape. In some embodiments, the animal model is a primate selected from the group consisting of a macaque, marmoset, tamarin, spider monkey, vervet monkey, squirrel monkey, and baboon. In some embodiments, the animal model is an ape selected from the group consisting of a gorilla, chimpanzee, orangutan, and gibbon. The animal model may be a hybrid of two non-human animals (e.g., dog-wolf). The animal model may have any desired genetic background. The animals may be crossed with many strains, and the genes may be studied with a wide genetic background, which is desired to recapitulate the complexity of cartilage degeneration.

In another embodiment of the present disclosure, there is described a method, performed by at least one computing device, for the diagnosis of cartilage degeneration, preferably facet cartilage degeneration, in a patient: (a) determining, at the processor, a sample RNA expression profile from RNA expression input for at least one of SEQ ID No. 1 and SEQ ID. NO. 2 based on a facet cartilage sample; (b) determining, by the processor, the statistical distance between the sample RNA expression profile and at least one of a degenerated facet cartilage reference profile and non-degenerated facet cartilage reference profile stored in a computer readable storage medium; wherein the statistical distance between the sample RNA expression profile and at least one of the degenerated facet cartilage reference profile and non-degenerated facet cartilage reference profile is associated with facet cartilage degeneration in the patient; (c) displaying a diagnosis of facet cartilage degeneration if the statistical distance is greater than a predetermined threshold statistical distance.

In yet another embodiment of the present disclosure, there is disclosed a system for the diagnosis of cartilage degeneration, preferably facet cartilage degeneration, in a patient: a non-transitory computer readable storage medium that stores computer-readable code; a processor operatively coupled to the non-transitory computer readable storage medium, the processor configured to implement the computer-readable code, the computer-readable code configured to: generate a sample RNA expression profile from RNA expression input for at least one of SEQ ID No. 1 and SEQ ID. NO. 2 based on a facet cartilage sample from the patient; compare the sample RNA expression profile to at least one of a degenerated facet cartilage reference profile and non-degenerated facet cartilage reference profile stored in a same or different non-transitory computer readable storage medium; calculate the statistical distance between the sample RNA expression profile and at least one of the degenerated facet cartilage reference profile and non-degenerated facet cartilage reference profile; wherein the statistical distance between the sample RNA expression profile and at least one of the degenerated facet cartilage reference profile and non-degenerated facet cartilage reference profile is associated with facet cartilage degeneration in the patient; and outputting a diagnosis of facet cartilage degeneration if the statistical distance is greater than a predetermined threshold statistical distance.

Figure 5:
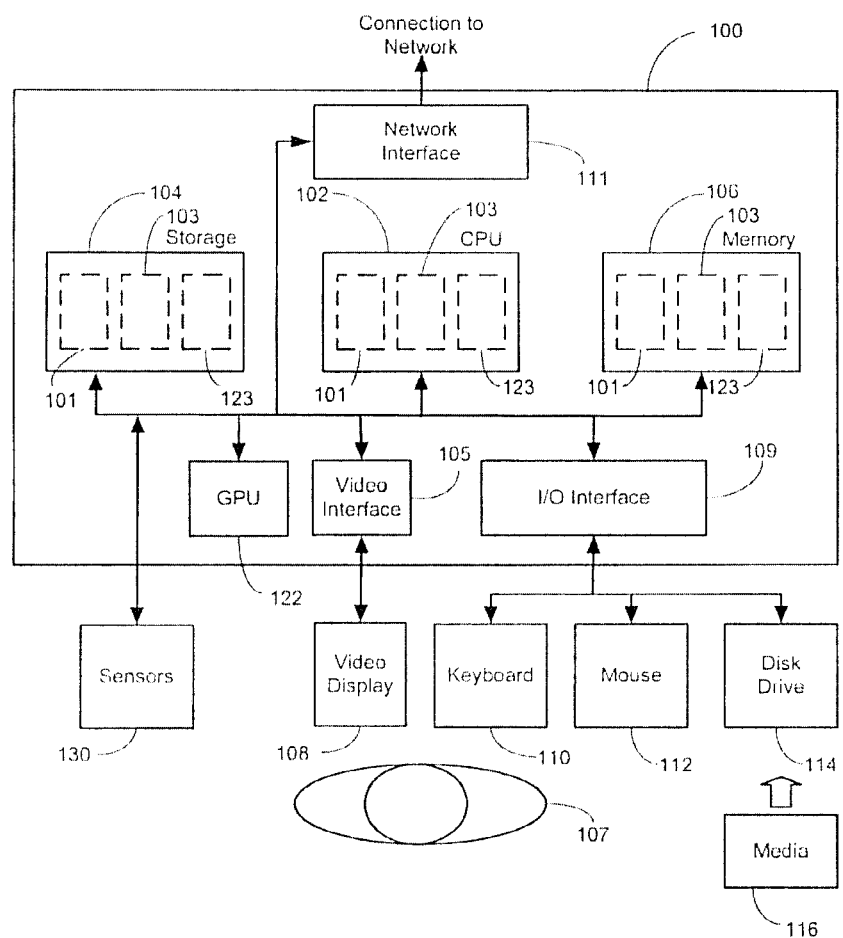
FIG. 5 shows a suitable configured computer device, and associated communications networks, devices, software and firmware to provide a platform for enabling one or more embodiments as described herein.

The present system and method may be practiced in various embodiments. A suitably configured computer device, and associated communications networks, devices, software and firmware may provide a platform for enabling one or more embodiments as described above. By way of example, FIG. 5 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

It will be appreciated by those skilled in the art that other variations of the embodiments described herein may also be practiced without departing from the scope of the invention. Other modifications are therefore possible.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

EXAMPLES

In this study we for the first time performed comprehensive screening and validation of 2,100 miRNAs in facet cartilage, and identified two miRNAs—miR-181a-5p and miR-4454—that were significantly up-regulated in FJ OA cartilage (exhibiting moderate to severe facet cartilage degeneration confirmed using MRI and histopathology) compared to control facet cartilage (lumbar disc herniation [LDH] patients exhibiting non to mild facet cartilage degeneration). We further tested if these two identified miRNAs (miR-181a-5p and miR-4454) play any pathophysiological role in facet cartilage degeneration. To identify the role of miR-181a-5p and miR-4454 in facet cartilage degeneration, we treated FJ OA chondrocytes with miR-181a-5p or miR-4454 mimic/inhibitor and showed that treatment with both miR-181a-5p or miR-4454 mimic significantly elevated the expression of inflammatory, catabolic and cell death markers and reduced expression of type II collagen. Cultured FJ OA chondrocytes treated with miR-181a-5p and miR-4454 inhibitors showed significant down-regulation in the expressions of catabolic, inflammatory and cell death markers but significant up-regulation in the expression of key extracellular matrix molecule, type II collagen, suggesting that miR-181a-5p and miR-4454 are key mediators of facet cartilage degeneration. Using computational biology approach, we also identified target genes and signaling pathways that may be modulated by these two miRNAs in facet cartilage. This study is the first to perform a comprehensive screening and identification of miR-181a-5p and miR-4454 as novel mediators of facet cartilage degeneration. By injecting miR-181a-5p mimic in rat FJs, we observed that the FJ OA phenotype is associated with enhanced catabolic activity and chondrocyte apoptosis in vivo.

We obtained facet cartilage from patients with FJ OA undergoing surgery for lumbar spinal canal stenosis (FJ OA group) and from patients with lumbar intervertebral disc herniation (LDH) (control group). Using these cohorts, we screened 2,100 miRNAs using miRNA-array analysis and differentially regulated microRNAs were further tested by RT-PCR analysis. FJ OA chondrocytes were cultured with/without IL-1β, and transfected with microRNA mimics/inhibitors (or control mimic/inhibitor) to determine the effect of miRNA enhancement/inhibition on the expression of catabolic/inflammatory, anabolic and cell death markers. Furthermore, target genes modulated by miRNAs were predicted using mirDIP[1] and pathway enrichment analysis was performed using pathDIP.

Out of 2,100 microRNA screened, we for the first time identified a panel of miRNAs that exhibited differential regulation in FJ OA cartilage compared to control cartilage. Further, validation specifically identified 2 microRNAs (miR-181a-5p and miR-4454) that were significantly up-regulated in FJ OA cartilage (n=34) compared to control facet cartilage (n=21). Cultured FJ OA chondrocytes treated with miR-181a-5p and miR-4454 mimics/inhibitors (compared to control mimic/inhibitor) showed significant up/down-regulation in the expressions of catabolic, anabolic, inflammatory and cell death markers.

Methods

Patient Information

The medial aspect of facet joints were obtained from spinal level L3-S1 of FJ OA patients (n=34; Age range: 42-81 years old, mean age±SEM: 65.5±1.6 years old) undergoing lumbar surgery for neurogenic claudication due to lumbar spinal canal stenosis (LSS) caused by FJ OA. In addition, facet joints were obtained from spinal level L4-S1 of LDH patients (n=21; Age range: 24-53 years old, mean age±SEM: 34.1±1.4 years old) undergoing microdiscectomy (control group). Patients with infection, other inflammatory or autoimmune diseases were excluded. The relevant surgical spine level(s) were determined from standard clinical and imaging assessment, as per standard surgical practice. The degree of degeneration in the facet joint and intervertebral disc on routine pre-operative MRIs was assessed and graded by two spine surgeons using the grading systems described by Weishaupt et al.[17] and Pfirrmann et al.[18], respectively (Table 1).

TABLE 1

Baseline characteristics and MRI grading assessment in control and facet joint osteoarthritis (FJ OA) groups.

|  | Control (n = 21) | FJ OA (n = 34) | |
|---|---|---|---|
| Age range (years old) | 24-53 | 42-81 | |
| Age mean ± SEM | 34.1 ± 1.4 | 65.5 ± 1.6 | **p < 0.01 |
| Male | 8 (38.1) | 16 (47.1) | |
| Female | 13 (61.9) | 18 (52.9) | |
| Surgical side | | | |
| Left | 13 (61.9) | 13 (38.2) | |
| Right | 8 (38.1) | 21 (61.8) | |
| Surgical level | | | |
| L 3/4 | 0 | 7 (20.6) | |
| L 4/5 | 7 (33.3) | 17 (50.0) | |
| L 5/S1 | 14 (66.7) | 10 (29.4) | |
| FJ degeneration grading | | | |
| 0 | 8 (38.1) | 0 | **p < 0.01 |
| 1 | 13 (61.9) | 0 | |
| 2 | 0 | 9 (26.5) | |
| 3 | 0 | 25 (73.5) | |
| Disc degeneration grading | | | |
| I | 0 | 0 | P = 0.78 |
| II | 1 (4.8) | 0 | |
| III | 7 (33.3) | 11 (32.4) | |
| IV | 9 (42.9) | 15 (44.1) | |
| V | 4 (19.0) | 8 (23.5) | |

No statistical differences in the severity of lumbar disc degeneration were observed in both groups (p = 0.78). The two-tailed Student's t test and the Chi-squared were used to analyze an age difference and gradings of FJ OA/disc degeneration in control vs. FJ OA groups, respectively.
FJ OA; facet joint osteoarthritis.

Histopathology

The degree of facet cartilage degeneration was determined by subjecting the FJs to histological analysis. Extracted FJ specimens from humans and rats were fixed in formalin for at least 72 hours, decalcified in 0.5M Hydrochloric acid (BioShop) with 0.1% Glutaraldehyde (Sigma-Aldrich) for 7 days for human samples and Rapid Decalcifier (Apex Engineering, Plainfield, Ill., USA) for 3 hours for rat samples, respectively, and embedded in paraffin. Serial sections (5-μm) were stained with Safranin O (Sigma-Aldrich)/Fast green (Bio Basic Canada Inc.) staining and evaluated by two blinded observers using the OARSI (Osteoarthritis Research Society International) grading score[19].

Immunohistochemistry and TUNEL Staining

Five micron sections were deparaffinised in xylene followed by a graded series of alcohol washes. Endogenous peroxide was blocked for 5 min using 1% $H_2O_2$ for 30 min. Non-specific IgG binding was blocked by incubating sections with bovine serum albumin (BSA) (0.1%) in PBS for 30 min. Sections were then incubated with primary antibodies, for PARP p85 (PROMEGA, Madison, Wis., USA, catalog # G734) (Dilution: 1:100), MMP13 (ABCAM, Toronto, ON, Canada, catalog # ab39012) (Dilution: 1:50) or rabbit IgG-HRP (Santa Cruz, Dallas, Tex., USA, catalog # sc2749) (Dilution: 1:50 or 1:100) as an isotype negative control in a humidified chamber and left overnight at 4° C. After washing twice in water, the slides were incubated with their respective biotinylated secondary antibodies for 30 min. Signal was amplified with HRP conjugated secondary antibody followed by Vectastain Elite ABC kit (Vector Laboratories), as per manufacturer's direction, and counterstained with eosin Y (Fisher Scientific). TUNEL assay was performed using ApopTag Plus Peroxidase In Situ Apoptosis Detection Kit (Millipore, Ontario, Canada, catalog # S7101) according to the manufacturer's directions. The quantification of the number of positive cells for each antigen was performed by counting of the total number of chondrocytes and the total number that stained positive for the antigen for at least 4 replicates. The final results were expressed as the percentage of positive cells for each antigen.

RNA Extraction from Human FJ Cartilage

For RNA extraction, fresh human FJ cartilage was immediately separated from the subchondral bone using a sterile scalpel blade and forceps under a dissection microscope (SMZ-168 Series, Motic). FJ cartilage was snap-frozen in liquid nitrogen and homogenized using the Cellcrusher tissue pulverizer (Cellcrusher), with the barrel and ball precooled in liquid nitrogen. The total RNA from FJ cartilage or chondrocytes was isolated using TRIzol reagent (Invitrogen) followed by RNeasy Mini kit clean-up (Qiagen), according to the manufacturers' protocols.

MicroRNA Microarray

Microarray and data analysis were conducted at Exiqon Services, Denmark. The miRNA profiling was performed using a seventh generation miRCURY LNA miRNA Array (Exiqon) containing capture probes targeting all human miRNAs annotated in miRBase 20.0. Four samples of total RNA extracted from facet cartilage (2 from FJ OA and 2 from control) were subjected to microRNA array. In FJ OA group, each sample consisted of pooled cartilage samples from n=3 separate FJ OA patients. Briefly, total RNA from FJ OA cartilage, isolated as described below, was used for hybridization; the quality of the total RNA was verified by an Agilent 2100 Bioanalyzer profile. 400 ng total RNA from each sample was labelled with Hy3 fluorescent label, using the miRCURY LNA miRNA Hi-Power Labelling Kit, Hy3/Hy5 (Exiqon). The Hy3-labelled samples and a Hy5-labelled reference RNA sample were mixed pair-wise and hybridized to the array. The hybridization was performed using a Tecan HS 4800 hybridization station (Tecan). The miRCURY LNA array slides were scanned using the Agilent G2565BA Microarray Scanner System (Agilent Technologies) and the image analysis was carried out using the ImaGene 9.0 software (Exiqon). The quantified signals were background corrected (Normexp with offset value 10) and normalized using the global Lowess (locally weighted scatterplot smoothing) regression algorithm. Following normalization, principal component analysis, traditional and matrix plots, and heat-map hierarchical clustering were obtained.

Reverse Transcription and Real-Time PCR (RT-PCR)

For RT-PCR, RNA concentrations were determined using Nano-Drop 1000 (Thermo Scientific) and NanoVue (GE Healthcare Life Science). Following RNA quantification, equal amounts of RNA (400 ng for mRNA and 10 ng for miRNA expression analysis) were converted to cDNA using the QuantiTect Reverse Transcription PCR Kit (Qiagen) for mRNAs or Universal cDNA synthesis kit II (Exiqon) for miRNAs, as per manufacturers' directions. For RT-PCR reactions, 5 ng of RNA per well was used for mRNA with primers and SYBR Green Master Mix (BIO-RAD), and 0.2 ng of RNA per well was used for miRNA with primers and SYBR Green Master Mix Kit (Exiqon) according to the manufactures' protocols. The reactions were incubated in 96 well plates (BIO-RAD) and all reactions were performed in duplicates. Specificity of the amplified RT-PCR product was assessed by performing melting curve analysis on the LightCycler® 480 Instrument. The relative expression of PCR products was calculated by the $2^{-\Delta Ct}$ method. All primers were designed using Primer3 online software (Table 2). Data were normalized to GAPDH for mRNAs and to hsa-U6 snRNA for miRNA analyses, respectively. Both reference genes showed highly stable expression compared to other candidates for reference genes. For some highly degenerated FJ OA cartilage specimens, pooled cartilage from at least two patient samples were used to extract adequate amount of RNA for RT-PCR analysis.

TABLE 2

Gene sequences of primers, mimics, and inhibitors for quantitative real-time PCR

| Genes | Forward primer (5'-3') | SEQ ID NO. | Reverse primer (5'-3') | SEQ ID NO. |
|---|---|---|---|---|
| GAPDH | CAGAACATCATCCCTGCCTCT | 7 | GCTTGACAAAGTGGTCGTTGAG | 23 |
| MMP13 | TCCCAGGAATTGGTGATAAGTAGA | 8 | CTGGCATGACGCGAACAAA | 24 |
| COL2A1 | TGGACGATCACGAAACC | 9 | GCTGCGGATGCTCTCAATCT | 25 |
| TNFA | GTCTCCTACCAGACCAAG | 10 | CAAAGTAGACCTGCCCAGACTC | 26 |
| IL6 | TGACAAACAAATTCGGTACATCCT | 11 | TCTGCCAGTGCCTCTTTGCT | 27 |
| MCP1 | CTCTGCCGCCCTTCTGTG | 12 | TGCATCTGGCTGAGCGAG | 28 |
| ANF440 | CATCATGCCCAGCTGCAACC | 13 | ATGGCACTGCTGGTTTTGGG | 29 |
| ZNF454 | TGCCTCCATAGCACTTTGCC | 14 | GCCACATCCTTGAAGGTCACC | 30 |
| MLL1 | ACTGTGGCGCCAAGAAATGC | 15 | TCAGCGTTGCTTTGGATGGC | 31 |
| KDM54 | TGTGCAAAAGGGGGAGAAGG | 16 | AACACTTGACGGCACACCTG | 32 |
| EIF4A2 | GAGCCACTTGTCATGCCTGC | 17 | ACACGACTTGACCCTGACCG | 33 |
| MBOAT2 | TGAAACAAGCCCTCCCATGC | 18 | ACGGACAAGTGCTGAGGTTG | 34 |
| ATM | CCAGCAAATTCTAGTGCCAGTCCAG | 19 | TGAGGTGGATTAGGAGCAGGATC | 35 |
| LRRC32 | TCAAGCGGCTCAATCTTGCC | 20 | TTGTTTCGCAGGTCCAGCAC | 36 |
| LARP4 | AGACCCGGAAGCAGTTGTTG | 21 | AAGGACACACACTCGCCTTG | 37 |
| CARD8 | GATGGAGTCGTAGGGGCCTGAG | 22 | CTCCCTCTCAGGGGCTTCACG | 38 | miRCURY LNA PCR primers (5'-3')

| | | |
|---|---|---|
| Hsa-miR-372-5p | CCUCAAAUGUGGAGCACUAUUCU | 39 |
| Hsa-miR-3156-5p | CCUGCAGAGAGGAAGCCCUUC | 40 |

TABLE 2-continued

Gene sequences of primers, mimics, and inhibitors for quantitative real-time PCR

| Genes | Forward primer (5'-3') | SEQ ID NO. | Reverse primer (5'-3') | SEQ ID NO. |
|---|---|---|---|---|
| Hsa-miR-711 | GGGACCCAGGGAGAGACGUAAG | 41 | | |
| Hsa-miR-4454 | GGAUCCGAGUCACGGCACCA | 42 | | |
| Hsa-miR-4534 | GGAUGGAGGAGGGGUCU | 43 | | |
| Hsa-miR-181a-5p | AACAUUCAACGCUGUCGGUGAGU | 44 | | |
| Hsa-miR-4484 | AAAAGGCGGGAGAAGCCCCCA | 45 | | |
| miRCURY LNA microRNA Mimic (5'-3') | | | | |
| Hsa-miR-181a-5p | AACAUUCAACGCUGUCGGUGAGU | 1 | | |
| Hsa-miR-4454 | GGAUCCGAGUCACGGCACCA | 2 | | |
| Hsa-miR-39-3p (control) | TCACCGGGTGTAAATCAGCTTG | 5 | | |
| miRCURY LNA Power Inhibitor (5'-3') | | | | |
| Hsa-miR-181a-5p | ACTCACCGACAGCGTTGAATG | 3 | | |
| Hsa-miR-4454 | TGGTGCCGTGACTCGGATC | 4 | | |
| Negative control | ATAACACGTCTATACGCCCA | 6 | | |

GAPDH: glyceraldehyde 3-phospate dehydrogenase, MMP13: metalloproteinase-13, COL2A1: type II collagen, TNFA: tumor recrosis factor-alpha, IL6: interleukin-6, MCP1: monocyte chemoattractant protein-1, ZNF440: zinc finger protein 440, ZNF454: zinc finger protein 454, MLL1: mixed-lineage leukemia 1, KDM5A: lysine demethylase 5A, EIF4A2: eukaryotic translation initiation factor 4A2, M5OAT2: membrane 4 bound O-acyltransferase domain containing 2, ATM: ATM serine/threonine kinase, LRRC32; leucine rich repeat containing 3, LARP4; la ribonucleoprotein domain family member 4, CARD8; caspase recruitment domain family member 8.

Facet Chondrocyte Cell Culture: Treatment with miRNA Mimics, or Inhibitors, or siRNA Chondrocytes were extracted from facet cartilage obtained from FJ OA patients as previously described.[20] Upon confluence, cells were plated at a density of $1 \times 10^5$ cells/well in six-well plates. For mimic studies, cells were treated with 5 nM miRCURY LNA Mimic for miR-181a-5p (hsa-miR-181a-5p), miR-4454 (hsa-miR-4454), or miR-39-3p (cel-miR-39-3p) (control) (Exiqon) for 24 hours using TransFectin™ Lipid Reagent (BIO-RAD) (1 µg/ml) according to the manufacturer's instructions. For inhibition, cells were treated with recombinant human IL-1β (10 ng/ml; R&D Systems) for 18 hours followed by transfection with 50 nM miRCURY LNA Power Inhibitor (antisense oligonucleotides) for miR-181a-5p or miR-4454 or scramble control A (Exiqon) for 24 hours. Total RNA and protein were isolated using TRIzol reagent (Invitrogen) or RIPA buffer (Sigma-Aldrich), respectively. Twenty four hours after seeding, first passage human facet chondrocytes were serum starved for 3 hours and co-transfected with miR-181a-5p or miR-4454 mimic (both at 5 nM) and ZNF440 siRNA (siZNF440) (50 nM) (Santa cruz, Dallas, Tex., USA, catalog # sc97725) or control siRNA (50 nM) (Qiagen, Valencia, Calif., USA, catalog #1027280; This siRNA has no homology to any known mammalian gene) using TransFectin™ Lipid Reagent (BIO-RAD) (10 µg/ml) in 0.5% of FBS and 1% Penicillin/Streptomycin media. After 48 hours of co-transfection, cells were washed 3 times with PBS and cell lysates were collected in RIPA buffer (Sigma-Aldrich).

miRNA Target and Pathway Enrichment Analysis

We used mirDIP[21] ver. 2.0 (ophid.utoronto.ca/mirDIP) to identify the most likely targets of miR-181a-5p and miR-4454, focusing only on mid-Third, top-Third and top 1% targets. Network was visualized using NAViGaTOR[22] ver 2.3 (ophid.utoronto.ca/navigator). Selected targets were then subjected to pathway enrichment analysis using pathDIP ver 1.0 (ophid.utoronto.ca/pathDIP).

Western Blot Analysis

Cells were lysed in RIPA buffer (Sigma-Aldrich) and applied to SDS-polyacrylamide gels (10%-15%) for electrophoresis. Separated proteins were electroblotted onto polyvinylidene fluoride membranes. Membranes were blocked in 10 mM Tris-buffered saline (TBS) containing 5% skimmed milk and probed for 1.5 hours with rabbit polyclonal IgG primary antibodies (1:500) specific for NF-κB p65 (Santa Cruz, Dallas, Tex., USA, catalog # sc109), phospho-NF-κB p65 (Ser536) (Cell Signaling, Danvers, Mass., USA, catalog #3031), IκBα (Santa Cruz, Dallas, Tex., USA, catalog # sc371), or PARP p85 (PROMEGA, Madison, Wis., USA, catalog # G734) or mouse monoclonal IgG (1:1000) for β-actin (Sigma-Aldrich, St. Louis, Mo., USA, catalog # A1978) in blocking buffer. After washing the membranes with TBS containing 0.1% Tween-20 (TBS-T) 3 times, the membranes were incubated overnight at 4° C. with HRP conjugated anti-rabbit (1:5,000; Sigma-Aldrich, St. Louis, Mo., USA, catalog # SAB3700843) or anti-mouse (1:10,000; Sigma-Aldrich, St. Louis, Mo., USA, catalog # A2179) secondary antibodies in TBS containing 5% skimmed milk. Membranes were subsequently washed in TBS-T, and protein bands were visualized with an enhanced chemiluminescence substrate (Clarify™ Western ECL Substrate, BIORAD and SuperSignal West Pico, Thermo Science) using a Bio-Rad Chemidoc Apparatus. Blots were scanned, and signal intensity was calculated using Image J (National Institutes of Health, USA).

Injection of miR-181a-5p into Lumbar FJs of Rats

Male Sprague-Dawley rats (200-220 g; n=7/group; Charles River, Canada) were anesthetized with 2.0% isoflurane in oxygen in a prone position. Following a 2-cm midline skin incision, right paraspinal muscles were retracted exposing the left L4/L5 and L5/L6 FJs (most common levels affected in lumbar FJ OA), and injected with intra-articular injection with miRCURY LNA mimic hsa-miR-181a-5p in vivo Ready (2 µl of 2.5 µg/µl; Exiqon) through the facet capsular tissue using a 26-gauge Hamilton syringe. Left FJs at identical levels were injected with miRCURY LNA mimic cel-miR-39-3p in vivo Ready (control mimic) (2 µl of 2.5 µg/µl; Exiqon). Rats in sham group only underwent surgical incision without injection. Rats were sacrificed at 3 weeks after surgery/injection for histological and immunohistochemical analysis.

The data supporting the results of miRNA screening (microarray) between FJ OA group and control group are available in the NCBI's Gene Expression Omnibus (GEO) repository (GEO accession: GSE79258) for facet cartilage miRNA array analysis (www.ncbi.nlm.nih.gov/geo/query/acc.cgi?acc=GSE79258).

Statistical Analysis

Data are presented as box-and-whiskers plots, with the horizontal lines and cross marks representing the medians and the means, respectively. The upper and lower bounds of the box correspond to the $25^{th}$ and $75^{th}$ percentiles of the dataset. The whiskers denote the minimum and maximum values of the dataset. The patient average age in control and FJ OA groups are presented as mean±SEM. Difference in the expression of miRNAs and mRNAs (isolated from FJ cartilage or FJ OA chondrocytes treated with miR-mimics) were analyzed by two-tailed Student's T test. Differences in the expression levels of markers in response to miR-181a-5p and miR-4454 inhibition with or without IL-1β and co-transfection with miRNA mimics and siRNA treatments were determined by One-way analysis of variance followed by Tukey's Honest Significant Difference post-hoc test. Ordinal logistic regression models were used to test correlation between the expression of miR-181a-5p or miR-4454 and severity of FJ OA based on MRI grading score. Correlations between miR-181a-5p or miR-4454 expression and FJ OA MRI grade were assessed with Spearman's rank-order correlation coefficient. The Chi-squared test was used to evaluate differences in FJ OA and disc degeneration between control and FJ OA groups. A value of $P<0.05$ was considered statistically significant for all comparison tests.

Study Approval

The human facet cartilage study was approved by the Institutional Research Ethics Board (REB) Committee. Informed consent to participate in this study was obtained from all patients. The animal experiments were approved by the Animal Resource Centre, University Health Network.

Results

Establishment of a Patient Cohort with Varying Degrees of Facet Cartilage Degeneration.

FJs were obtained from L3-S1 spinal levels of FJ OA patients undergoing lumbar surgery for neurogenic claudication (n=34; age range: 42-81 years old, mean age±SEM: 65.5±1.6 years old) due to lumbar spinal stenosis (LSS) or radiculopathy (n=21; age range: 24-53 years old, mean age±SEM: 34.1±1.4 years old) due to lumbar disc herniation (LDH).

At the surgical level, the degree of FJ and intervertebral disc degeneration was assessed using MRI as described by Weishaupt et al.[17] and Pfirrmann et al.[18], respectively (FIG. 1A and Table 1). The FJs in all patients from the LDH group exhibited a degenerative grade of 0 (normal; 38.1%) or 1 (mild; 61.9%) and thus formed our control group. Whereas all patients with surgery for LSS exhibited significant greater FJ OA ($P<0.01$): 26.5% of patients had grade 2 (moderate) FJ OA and 73.5% had grade 3 (severe) FJ OA (Table.1). No statistical difference ($P=0.78$) in the degree of intervertebral disc degeneration were observed between two groups. Qualitative histological analysis further showed normal or mild facet cartilage degeneration, proteoglycan loss and loss of cellularity in control facet cartilage, whereas moderate to severe facet cartilage degeneration was observed in FJ OA cartilage with profound loss of proteoglycan and chondrocytes. OARSI (Osteoarthritis Research Society International) scoring, measured on a scale from 0-6[19], showed significantly increased ($p<0.01$) cartilage degeneration in facet cartilage from the FJ OA group: compared to the control group (Figure. 1B). Taken together, clinical imaging and histological analysis clearly show an enhanced degree of facet cartilage degeneration in the FJ OA group compared to the control group.

Expression of Catabolic, Inflammatory, Cell Death Markers and Type II Collagen in FJ OA Cartilage Compared to Control Cartilage After confirming that facet cartilage degeneration in FJ OA patients exhibited greater severity, as assessed by MRI and histopathology, we next determined the expression of key catabolic, inflammatory, cell death markers and cartilage matrix molecule (type II collagen) implicated in cartilage degeneration during OA pathogenesis in FJ OA cartilage compared to control cartilage. Real-time PCR (RT-PCR) analysis showed, that compared with control cartilage, FJ OA cartilage exhibited an increase in the expression of major cartilage catabolic factor matrix metalloproteinase-13 (MMP-13) ($P<0.01$), and pro-inflammatory cytokines, such as TNFA ($P<0.05$), IL6 ($P<0.05$) and monocyte chemoattractant protein-1 (MCP1) ($P<0.01$), and a decrease in the expression of type II collagen mRNA (COL2A1) ($P<0.05$), whose protein product is a major contributor to the cartilage matrix (FIG. 1C). Furthermore, increased chondrocyte death/apoptosis was observed in FJ OA cartilage compared with control cartilage, as assessed by TUNEL and poly ADP-ribose polymerase (PARP) p85 immunostaining (FIG. 1D). These results show enhanced catabolic, inflammatory and chondrocyte cell death activity in chondrocytes and decreased anabolic activity in FJ OA cartilage compared to control cartilage.

miRNA Screening Phase: Identification of a Panel of miRNAs that are Differentially Expressed in FJ OA Cartilage Compared with Control Cartilage We next comprehensively screened the expression of miRNA species in phenotypically distinct facet cartilage (FIG. 2A). Out of 2,100 miRNAs screened using miRNA array, we identified a panel of miRNAs that were differentially expressed in the FJ OA cartilage (n=2; each sample consisted of pooled cartilage specimens from n=3 patients of similar MRI grade; FJ OA sample 1: grade 2, FJ OA sample 2: grade 3) compared with control facet cartilage (n=2) (grade 0). Out of 2100 miRNAs, 22 miRNAs showed greater than 1.5 fold change (up-regulation or down-regulation) and 7 miRNA showed greater than 2 fold change in FJ OA cartilage compared to control cartilage (FIG. 2B). Microarray data is accessible at www.ncbi.nlm.nih.gov/geo/query/acc.cgi?acc=GSE79258.

Validation Phase: Elevated Expression of miR-181a-5p and miR-4454 in FJ OA Cartilage For validation phase, miRNAs exhibited greater than a 2-fold change in their expression between FJ OA cartilage compared with control cartilage, including hsa-miR-372-5p, hsa-miR-3158-5p, hsa-miR-711, hsa-miR-4454, hsa-miR-4534, hsa-miR-181a-5p and hsa-miR-4484, were further subjected to RT-PCR analysis in n=34 FJ OA cartilage samples and n=21 control cartilage samples. Results showed that, of 7 miRNAs tested, only miR-181a-5p and miR-4454 were significantly up-regulated (p<0.01) in FJ OA cartilage (n=34) compared to control facet cartilage (n=21) (FIG. 2C), with no significant differences in the expressions of other 5 miRNAs was observed (Table 3).

TABLE 3

Seven microRNAs (miRNAs) identified during screening phase (exhibiting ≥ 2.0-fold change in the expression) were further validated by real-time PCR (RT-PCR) in n = 21 control and n = 34 FJ OA cartilage.

| MicroRNAs | Screening phase (microRNA array) | | | Validation phase |
|---|---|---|---|---|
| | Mean fold change | | Up or Down | (RT-PCR) |
| (≥2.0-fold) | Control | FJ OA | regulation | P value |
| miR-372-5p | 1 | −2.99495 | ↓ | 0.154 |
| miR-3158-5p | 1 | −2.38262 | ↓ | 0.647 |
| miR-711 | 1 | −2.26024 | ↓ | 0.256 |
| miR-4454 | 1 | 2.249572 | ↑ | <0.01** |
| miR-4534 | 1 | −2.16688 | ↓ | 0.167 |
| miR-181a-5p | 1 | 2.150419 | ↑ | <0.01** |
| miR-4484 | 1 | −2.13305 | ↓ | 0.353 |

**$p < 0.01$, as determined using two-tailed Student's T test.

Further, ordinal logistic regression analysis showed a significant positive correlation between the expressions of miR-181a-5p (p=0.0082) or miR-4454 (p=0.0061) and the severity of FJ OA based on MRI clinical grading score (FIG. 2D) (correlation coefficients were 0.42 for miR-181a-5p expression and 0.46 for miR-4454 expression; Table 4). For miR-181a-5p, a 1-unit increase in the expression was associated with a 3.2-fold increase in odds of a higher FJ OA grade. For miR-4454, a 1-unit increase in the expression was associated with a 2.0-fold increase in odds of a higher FJ OA grade.

TABLE 4

Result of Ordinal logistic regression models of FJ OA grade assess by MRI grading scale (0, 1, 2, or 3) and Spearman's rank correlations between miRNA expression and FJ OA grade in 55 subjects.

| | miR-181a-5p | miR-4454 |
|---|---|---|
| Odds ratio for increased grade | 3.237073 | 2.0454479 |
| p value* | 0.008188489 | 0.006106278 |
| AIC | 139.2706 | 139.3924 |
| Spearman's rank correlation | 0.424 | 0.460 |
| | (p = 0.0012†) | (p = 0.0004†) |

Figure 3C:
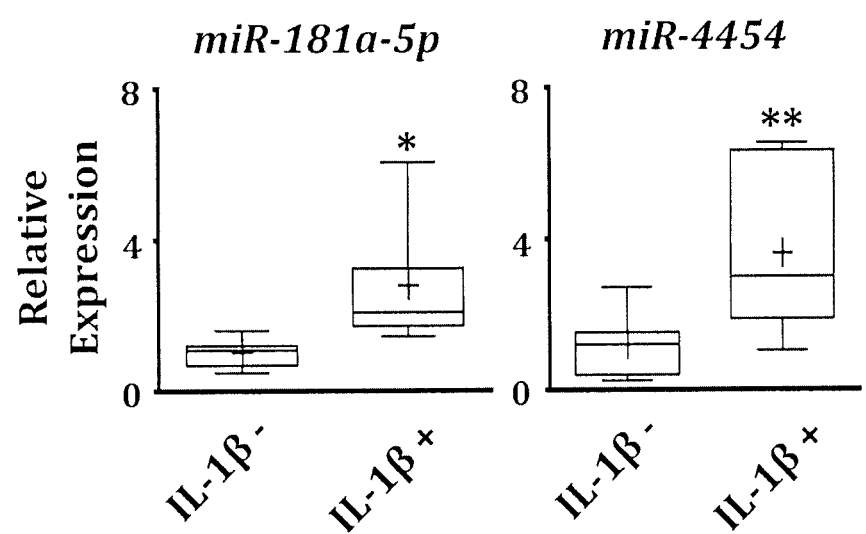
Figures 3D, 3E:
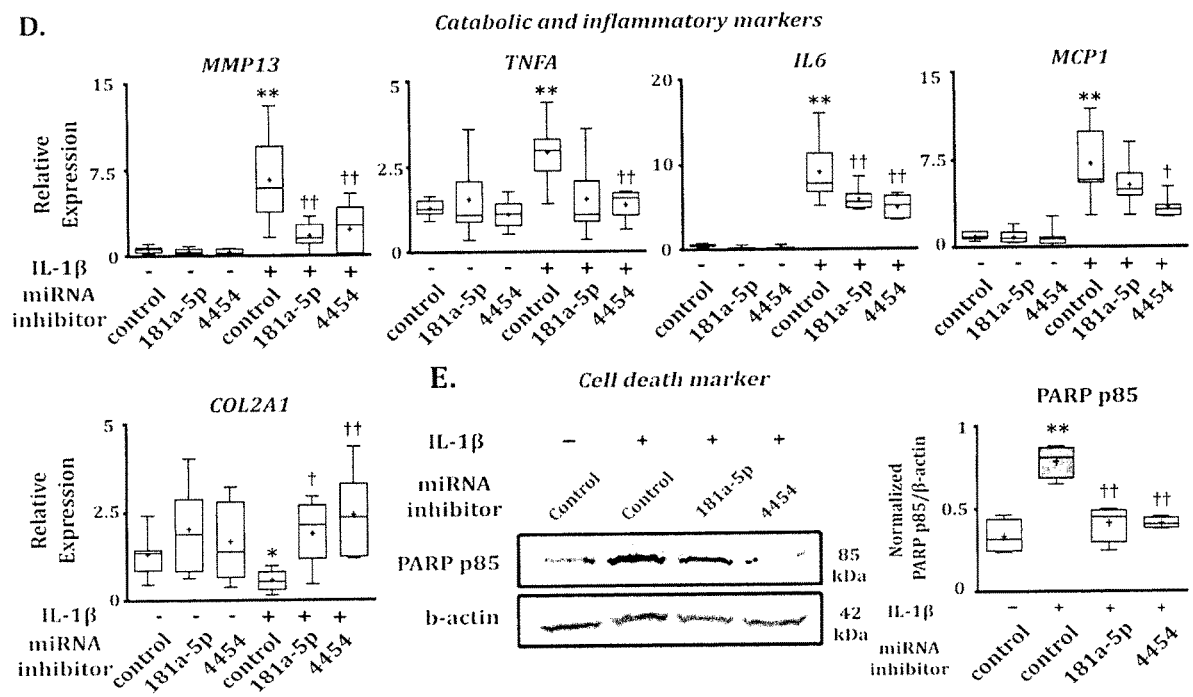

Correlations between miRNA expression and FJ OA grade were assessed with Spearman's rank-order correlation coefficient. The correlation coefficients were 0.42 for miR-181a-5p expression and 0.46 for miR-4454 expression; both were statistically significant.
AIC; Akaike information criterion.
*null hypothesis. OR = 1
†null hypothesis: correlation coefficient = 0 miR-181a-5p and miR-4454 Mimics Increase the Expression of Catabolic, Inflammatory and Cell Death Markers and Suppress Type II Collagen Expression in FJ OA Chondrocytes After confirming that miR-181a-5p and miR-4454 are significantly elevated in FJ OA cartilage compared to control cartilage, we further investigated if these miRNAs play a role in facet cartilage degeneration. Facet chondrocytes from FJ OA cartilage (n=6/group) were treated with miR-181a-5p mimic or miR-4454 mimic, or control mimic. We observed a significant increase in the mRNA expression of catabolic (MMP13) and inflammatory markers (TNFA, and MCP1), and protein expression of cell death marker (PARP p85) in facet chondrocytes treated with miR-181a-5p mimic (FIGS. 3 A and B). Facet chondrocytes treated with miR-4454 mimic also showed a significant increase in the expression of TNFA, 1L6, MCP1 and PARP p85, but no significant increase in the expression of MMP13. Furthermore, we observed a significant decrease in the expression of COL2A1 in FJ OA chondrocytes treated with either miR-181a-5p or miR-4454 mimic compared to the control mimic, suggesting that miR-181a-5p and miR-4454 promote catabolic, inflammatory and cell death activity and suppress anabolic activity of FJ OA chondrocytes.

miR-181a-5p and miR-4454 Inhibition Suppress the Expression of Catabolic, Inflammatory and Cell Death Markers and Elevate Type II Collagen Expression in 1-1p-Treated FJ OA Chondrocytes Since miR-181a-5p and miR-4454 mimics increased expression of catabolic, inflammatory and cell death markers and reduced the expression of COL2A1, we further tested if inhibition of these miRNAs can reverse these effects. As IL-1β is the major inflammatory/catabolic cytokine implicated in OA, FJ OA chondrocytes were treated with/without recombinant human IL-1β in the presence of miR-181a-5p, miR-4454 or control inhibitor. The expression of both miR-181a-5p and miR-4454 was significantly enhanced in response to IL-1β treatment (FIG. 3C). Furthermore, IL-1β treatment significantly increased the expression of MMP13 and significantly reduced the expression of COL2A1 (FIG. 3D). Treatment with either miR-181a-5p or miR-4454 inhibitor significantly suppressed MMP13 and rescued the expression of COL2A1 in IL-1β-treated cells. These results show that inhibition of miR-181a-5p or miR-4454 in IL-1β treated FJ OA chondrocytes leads to a decrease in catabolic activity and increased anabolic activity.

We then assessed whether miR-181a-5p and miR-4454 inhibition could suppress the expression of inflammatory mediators in IL-1β-stimulated FJ OA chondrocytes. IL-1β treatment significantly elevated the expression of IL6, TNFA and MCP1 in FJ OA chondrocytes. Inhibition of either miR-181a-5p or miR-4454 significantly suppressed the expression of IL6 (FIG. 3D). However, the expression of TNFA and MCP1 were significantly suppressed only by the miR-4454 inhibitor and not by the miR-181a-5p inhibitor. These results show that inhibition of miR-181a-5p or miR-4454 results in differential suppression of inflammatory mediators.

We further determined the effect of miR-181a-5p and miR-4454 inhibition on the level of PARP p85 in IL-1β-stimulated FJ OA chondrocytes. IL-1β treatment-mediated increases in the protein levels of PARP p85 were inhibited by both miR-181a-5p and miR-4454 inhibitors (FIG. 3E). We have summarized the specific effects of the miR-181a-5p and miR-4454 mimics and inhibitors on the expression of inflammatory, catabolic, cell death and cartilage matrix markers in Table 5.

TABLE 5

A summary of up-regulation or down-regulation in the expression of inflammatory, catabolic, anabolic and cell death mediators in facet joint osteoarthritis (FJ OA) chondrocytes treated with microRNA (miR) 181a-5p or miR-4454 mimic/inhibitor.

|  |  | Inflammatory mediators | | | Catabolic mediator | Cartilage Matrix Molecule | Cell death Mediator |
|---|---|---|---|---|---|---|---|
| miRNAs treatment | | TNFA | IL6 | MCP1 | MMP13 | COL2A1 | PARP p85 |
| mimics | miR-181a-5p | ↑ | ↑ | ↑ | ↑ | ↓ | ↑ |
|  | miR-4454 | ↑ | ↑ | ↑ | NS | ↓ | ↑ |
| Inhibitors | miR-181a-5p | NS | ↓ | NS | ↓ | ↑ | ↓ |
|  | miR-4454 | ↓ | ↓ | ↓ | ↓ | ↑ | ↓ |

TNFA; tumor necrosis factor-alpha, IL6; interleukin-6, MCP1; monocyte chemoattractant protein-1, MMP13; metalloproteinase-13, COL2A1; type II collagen, PARP p85; poly (ADP-ribose) polymerase, NS; not significant.

Signaling Pathways Modulated by miR-181a-5p and miR-4454

We applied an integrative, computational biology approach to predict gene targets and signaling pathways regulated by miR-181a-5p and miR-4454. Potential target genes for miR-181a-5p and miR-4454 were identified using mirDIP, focusing only on the middle third, top third, and top 1% targets (FIG. 4A). Taking the most likely targets of miR-181a-5p and miR-4454, we then identified the most frequently enriched pathways using pathDIP. While 247 pathways were significantly enriched, we identified the most frequent pathways associated with both miR-181a-5p and miR-4454. Specifically, the top 1% of individual target genes were related to the NFκB signaling pathways.

To test these predictions, we treated FJ OA chondrocytes with miR-181a-5p mimic, miR-4454 mimic, or control mimic and determined the expression of the 10 predicted genes [zinc finger protein 454 (ZNF454), zinc finger protein 440 (ZNF440), mixed-lineage leukemia 1 (MLL1), lysine demethylase 5A (KDM5A), eukaryotic translation initiation factor 4A2 (EIF4A2), membrane bound O-acyltransferase domain containing 2 (MBOAT2), ATM serine/threonine kinase (ATM), leucine rich repeat containing 32 (LRRC32), la ribonucleoprotein domain family member 4 (LARP4), caspase recruitment domain family member 8 (CARD8)] regulated by both miR-181a-5p and miR-4454. Results showed that out of all 10 genes tested, 8 genes did not exhibit any significant differences in their expression in response to miR-181a-5p or miR-4454 mimic in FJ OA chondrocytes. Interestingly, expression of ZNF440 was significantly increased by both miR-181a-5p and miR-4454 mimic compared to control mimic (FIG. 4B). The expression of MBOAT2 was only elevated in response to miR-181a-5p mimic (Table 6).

TABLE 6

Relative expression of predicted target gene candidates associated with both microRNA (miR)-181a-5p and miR-4454 assessed by real-time PCR (RT-PCR) analysis

| Gene | Control mimic | miR-181a-5p mimic (P value compared to control) | miR-4454 mimic (P value compared to control) |
|---|---|---|---|
| ZNF454 | 0.50 ± 0.03 | 0.51 ± 0.04 (0.90) | 0.60 ± 0.12 (0.45) |
| ZNF440 | 0.39 ± 0.06 | 0.69 ± 0.07 (0.01*) | 0.91 ± 0.20 (0.04*) |
| MLL1 | 0.44 ± 0.04 | 0.46 ± 0.04 (0.76) | 0.42 ± 0.02 (0.68) |
| KDM5A | 0.49 ± 0.12 | 0.51 ± 0.11 (0.92) | 0.76 ± 0.18 (0.25) |
| EIF4A2 | 1.00 ± 0.12 | 1.27 ± 0.10 (0.12) | 0.85 ± 0.10 (0.36) |
| MBOAT2 | 0.46 ± 0.03 | 0.57 ± 0.03 (0.04*) | 0.49 ± 0.06 (0.62) |
| ATM | 0.40 ± 0.05 | 0.39 ± 0.03 (0.93) | 0.35 ± 0.02 (0.38) |
| LRRC32 | 0.70 ± 0.17 | 0.62 ± 0.10 (0.69) | 0.81 ± 0.14 (0.63) |
| LARP4 | 0.35 ± 0.06 | 0.37 ± 0.05 (0.81) | 0.48 ± 0.07 (0.17) |
| CARD8 | 0.87 ± 0.22 | 0.98 ± 0.20 (0.72) | 1.14 ± 0.23 (0.41) |

Each relative expression in RT-PCR products was calculated by the $2^{-\Delta Ct}$ method. Data were normalized to glyceraldehyde 3-phosphate dehydrogenase (GAPDH). The data are expressed as mean ± SEM.
*p < 0.05. The significance between control mimic and miR-181a-5p or miR-4454 mimic treatments was determined using a multiple Student's T test.

Figure 4G:
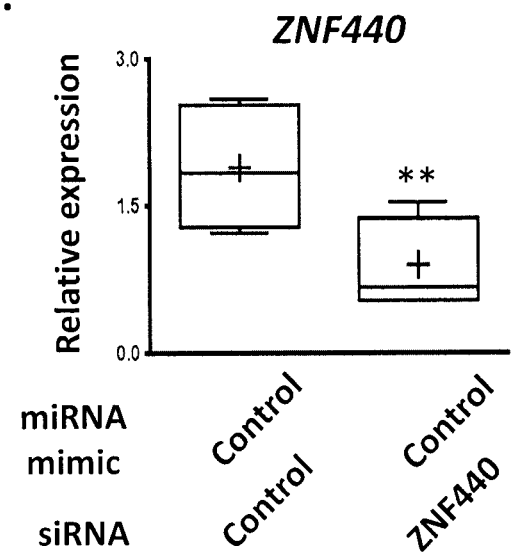
FIG. 4 shows miR-181a-5p and 4454 target genes. (A) Potential target genes for miR-181a-5p and miR-4454 were identified using mirDIP ver. 2, focusing only on midThird, topThird and top 1% of targets. miRNA gene network was visualized using NAViGaTOR ver. 2.3. The network highlights shared targets (central nodes in the network), and individual target predictions (left and right lists). Thick red edge signifies top 1% of prediction (corresponding genes are highlighted with red outline and name); purple edge signifies top Third predictions; all other edges correspond to mid-Third predictions. Highlighted shared targets predicted with top-Third hits. (B) RT-PCR analysis of zinc finger 440 (ZNF440) expression in FJ OA chondrocytes treated with miR-181a-5p or miR-4454 mimic compared to control mimic (n=6/treatment). *, p<0.05, comparing control mimic vs. miR-181a-5p or miR-4454 mimic, as determined by two-tailed Student's T tests. (C) RT-PCR analysis ZNF440 expression of FJ chondrocytes treated with (+) or without (−) IL-1β and miR-181a-5p, miR-4454 or control inhibitors (n=7/treatment). Data were analyzed by one-way analysis of variance followed by Tukey's post-hoc tests. **, p<0.01, control inhibitor with IL-1β vs control inhibitor without IL-1β treatment; †, p<0.05 or ††, p<0.01, control inhibitor vs miR-181a-5p or miR-4454 inhibitor in the presence of IL-1β, respectively. All other comparisons were not significantly different (p>0.05), (D) The most significantly enriched pathway for miR-181a-5p and miR-4454 targets include NF-κB pathways, as identified using pathDIP ver 1.0. (E) Immunoblot analysis of phosphorylation of Ser536 on NF-κB-p65 (p-p65) in FJ OA chondrocytes treated with (+) or without (−) IL-1β. (F) Immunoblot analysis of p-p65 and IκBα in FJ OA chondrocytes treated with miR-181a-5p, miR-4454 or control mimics. (E&F) Representative blot from n=4 separate blots. *, p<0.05,**, p<0.01, compared to untreated or control mimic as determined by two-tailed Student's T-test. (G) Expression of ZNF440 in facet joint osteoarthritis (FJ OA) chondrocytes co-transfected with control miRNA mimic and control siRNA or control miRNA mimic and ZNF440 siRNA (n=5/each group). The result showed a significant decrease in the expression of ZNF440 in FJ OA chondrocytes transfected with ZNF440 siRNA compared to control siRNA. (H) Immunoblot analysis of p-p65 in response to miR-181a-5p mimic or miR-4454 mimic and/or ZNF440 siRNA. Representative blot from n=4 separate blots. Differences in groups were analyzed by one-way analysis of variance followed by Tukey's post-hoc tests. *, p<0.05, control mimic/control siRNA vs miR-181a-5p mimic/control siRNA or miR-4454 mimic/control siRNA, †, p<0.05, miR-181a-5p mimic/control siRNA vs miR-181a-5p/ZNF440 siRNA treatment. ¶, p<0.05, miR-4454 mimic/control siRNA vs miR-4454 mimic/ZNF siRNA treatment. All other comparisons were not significantly different (p>0.05). Data presented as box-and-whiskers plots. Horizontal lines and cross marks indicate the medians and the means, boxes indicate 25th to 75th percentiles, and whiskers indicate minimum and maximum values of the dataset.

To further test the involvement of ZNF440 in miR-181a-5p and miR-4454 signaling, we next treated FJ OA chondrocytes with IL-1β in the presence/absence of miR-181a-5p or miR-4454 inhibitor. IL-1β significantly increased the expression of ZNF440 and this expression was significantly suppressed by both miR-181a-5p and miR-4454 inhibitors (FIG. 4C), suggesting that ZNF440 may play a role in miR-181a-5p and miR-4454 signaling in facet chondrocytes. Based on our prediction data, the NF-κB signaling pathway showed significant association with both miR-181a-5p and miR-4454 (FIG. 4D). NF-κB is negatively regulated by IκB, which retains NF-κB in the cytoplasm inhibiting its transcriptional activity [canonical, IκB-dependent regulation;[23]] whereas phosphorylation of NF-κB p-65 on Ser536 renders NF-κB p-65 active irrespective of IκB expression [IκB-independent regulation[24]]. We first determined the phosphorylation of Ser536 of the NF-κB p-65 subunit, a marker of IκB-independent activity, in FJ OA chondrocytes treated with IL-1β. IL-1β treatment resulted in increased phosphorylation of Ser536 NF-κB p65 in FJ OA chondrocytes (FIG. 4E). Furthermore, treatment with miR-181a-5p or miR-4454 mimic alone significantly enhanced the phosphorylation of Ser536 NF-κB p65. Interestingly, miR-181a-5p or miR-4454 mimic also decreased the expression of IκBα in chondrocytes (FIG. 4F), suggesting that NF-κB activity can be modulated by miR-181a-5p or miR-4454 by regulating both IκB-dependent and -independent NF-κB regulatory pathways. To further explore the role of ZNF440 on IκB-independent NF-κB p-65 activation in response to miR-181a-5p and miR-4454 signaling, we co-transfected FJ OA chondrocytes with either miR-181a-5p or miR-4454 mimic in the absence/presence of ZNF440 siRNA to determine the effect of silencing ZNF440 on the phosphorylation of Ser536 of NF-κB p65. Co-transfection of chondrocytes with ZNF440 siRNA resulted in a significant knockdown in the expression of ZNF440 (FIG. 4G).

Figure 4H:
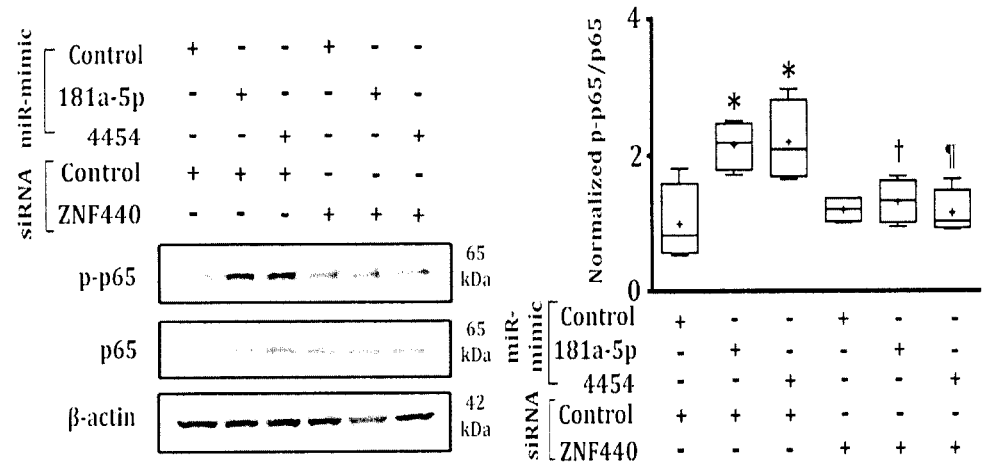

Further, as expected, western blot analysis showed an increased phosphorylation of Ser536 NF-κB p65 in response to miR-181a-5p or miR4454 mimic in the presence of control siRNA; however, these increases in phosphorylation of Ser536 NF-κB p65 were attenuated by ZNF440 siRNA (FIG. 4H), suggesting a crucial role of ZNF440 in regulating IκB-independent NF-κB signaling downstream of miR-181a-5p and miR-4454 in FJ OA chondrocytes.

miR-181a-5p Mimic Promotes Facet Cartilage Degeneration In Vivo

Figure 6:
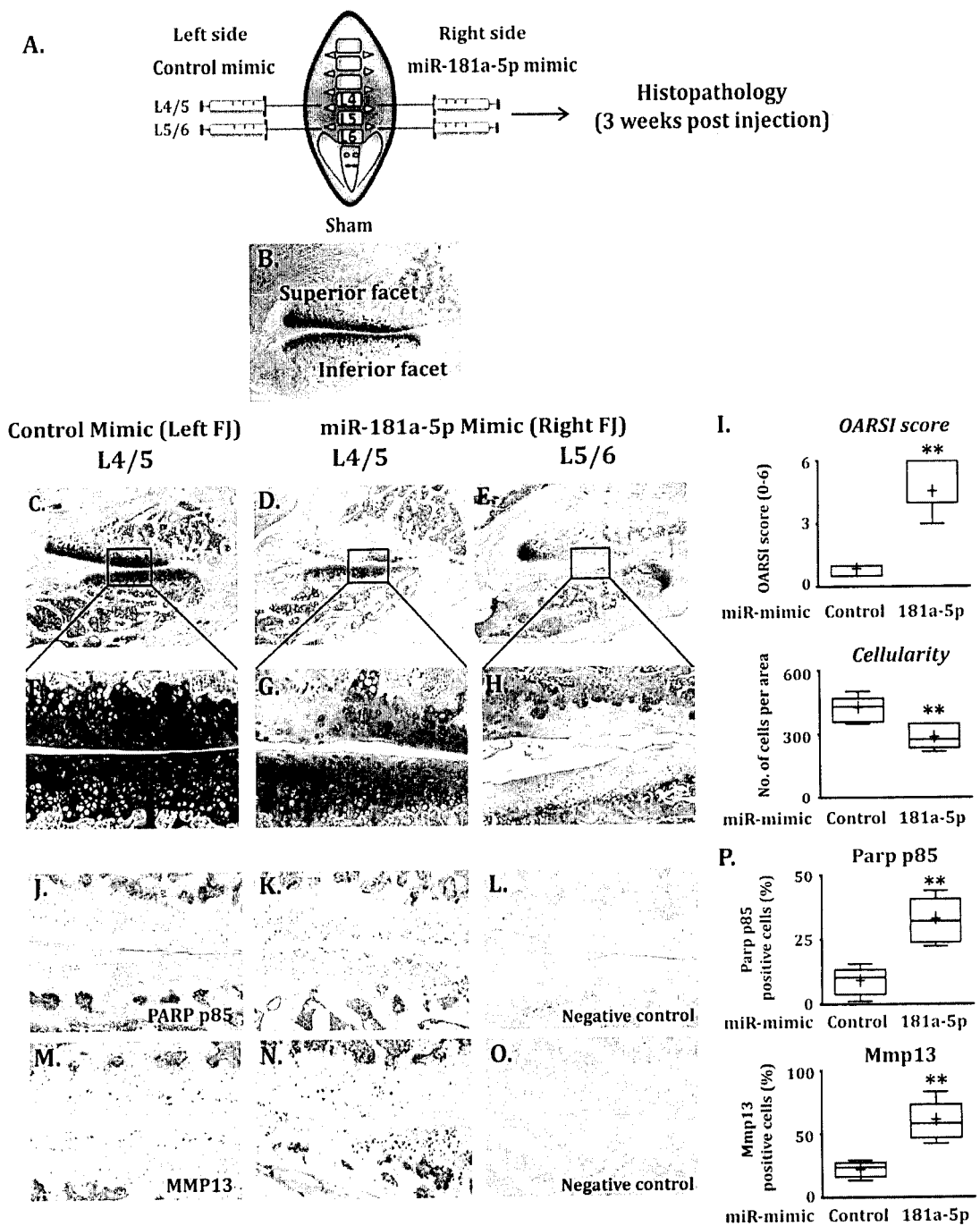
FIG. 6 shows miR-181a-5p mimic promotes cartilage degeneration in vivo. (A) Schematic of miR-181a-5p mimic injection in FJs of rat. miR-181a-5p mimic (right side; n=7) or control mimic (left side; n=7 were injected into two lumbar spinal facet joints (FJs) (L4/5 and L5/6) using a 26 gauge Hamilton syringe under surgical microscope. (B-H) Rat FJ (L4/5 and L5/6) stained with Safranin 0/fast green stain: miR-181a-5p mimic injection resulted in FJ OA like phenotype associated with loss of chondrocyte cellularity, proteoglycan depletion and cartilage degeneration in vivo. (B) Sham: without injection, (C&F) L4/5 FJ treated with control mimic, (D&G) L4/5 FJ treated with miR-181a-5p mimic, (E&H) L5/6 FJ treated with miR-181a-5p mimic. (B-E: 4× magnification, F-H: 20× magnification). (I) Histomorphometric analysis of FJs treated with miR-181a-5p or control mimic was scored by Osteoarthritis Research Society International (OARSI) scoring. Facet chondrocyte cellularity per area was calculated in FJs treated with miR-181a-5p or control mimic (n=7/each group). (J-P) Representative images of FJ cartilage sections analyzed by immunohistochemistry for Poly (ADP-ribose) polymerase p85 (PARP p85) or matrix metallopeptidase 13 (MMP13) (n=7/each group). (P) Immuno-positive and Total cells in FJ cartilage were counted and expressed as a percentage (%) of PARP p85 and MMP-13 positive cells. (L&O) Rabbit IgG-HRP was used as an isotype negative control. (20× magnification). (I&P) Data presented as box-and-whiskers plots. Horizontal lines and cross marks indicate the medians and the means, boxes indicate 25th to 75th percentiles, and whiskers indicate minimum and maximum values of the dataset. **, p<0.01, as determined by two-tailed Student's T-tests.
Figure 7A:
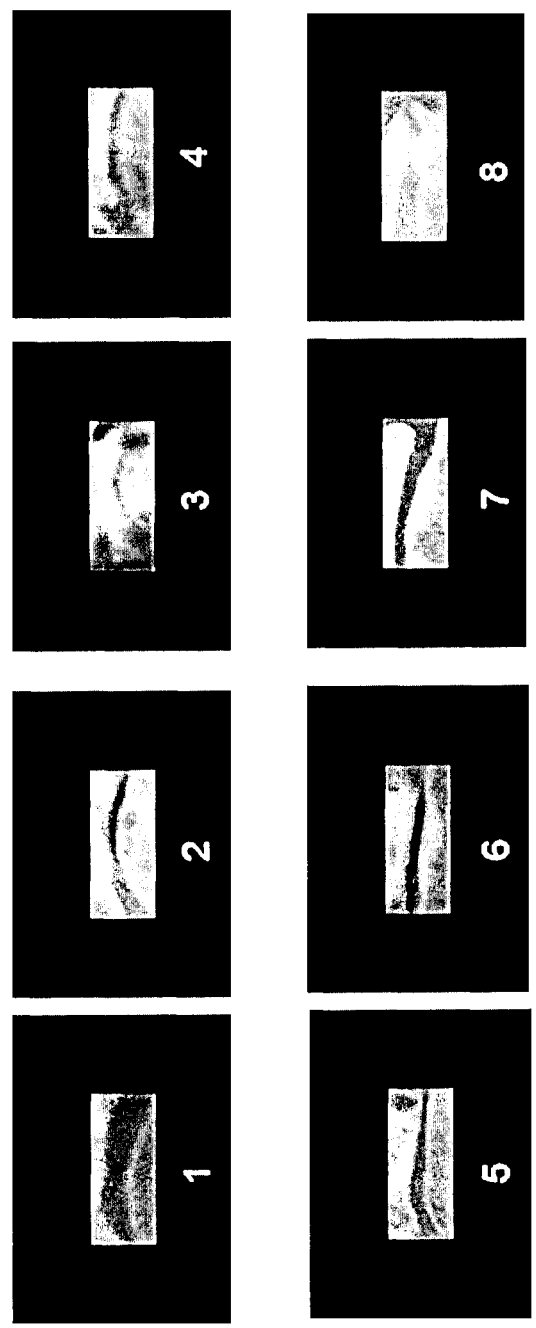
FIG. 7 shows (A) Representative Computed Tomographs (CTs) of appendicular joints, lumbar spine facets and disc, demonstrating similar subchondral changes. (B) Corresponding joints with OA: 1-Glenohumeral; 2-Tibio-talar (Ankle); 3-Lumbar Facet; 4-Hip; 5-Tibio-talar; 6-Lumbar Disc; 7-Knee; 8-Lumbar Disc.
Figure 7B:
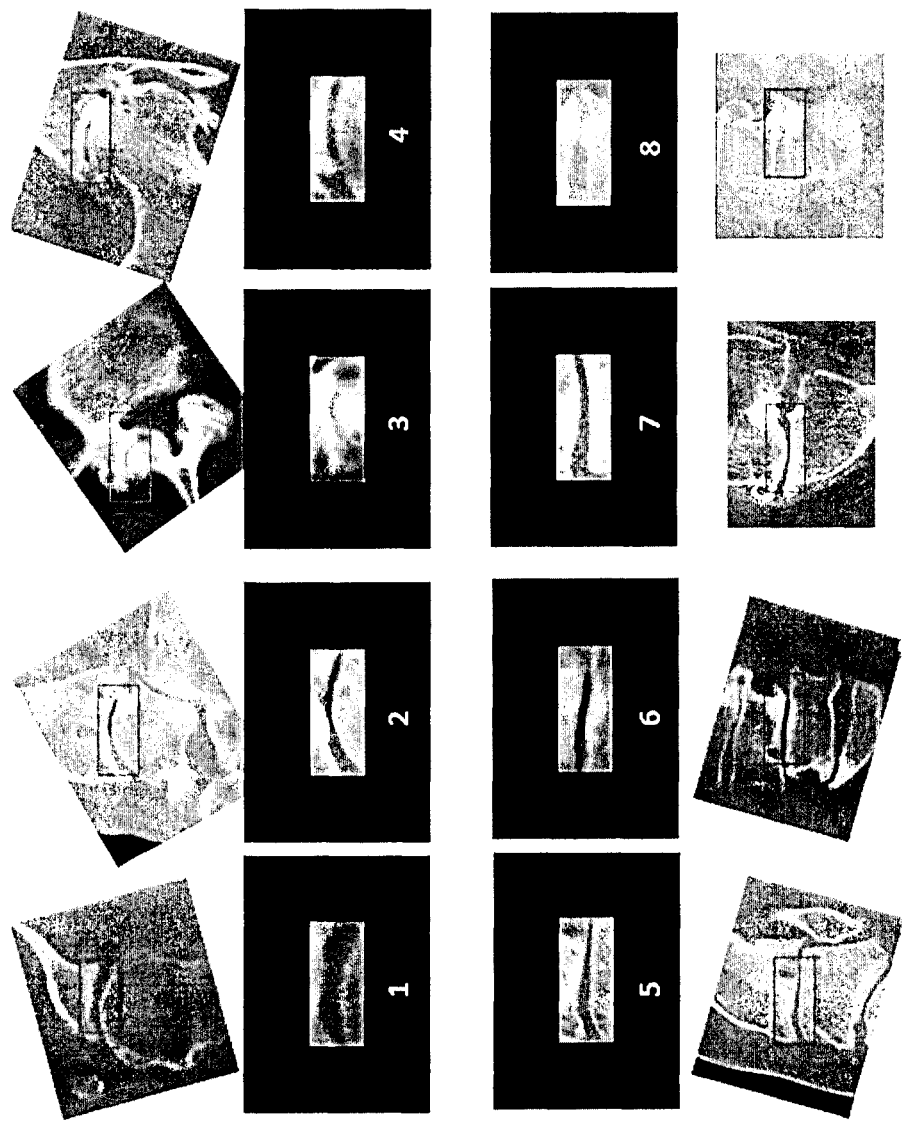

Our in vitro studies using FJ OA chondrocytes treated with miR-181a-5p or miR-4454 mimic or inhibitor suggest that these miRNAs may play a key role in facet cartilage degeneration by promoting catabolic, inflammatory and cell death mechanisms. The next logical step was to test if these miRNAs initiate cartilage destructive activity in vivo. Currently, no in vivo grade mimic for miR-4454 is commercially available. Therefore, we used in vivo grade miR-181a-5p mimic for our animal studies. We injected miR-181a-5p mimic (right side) or control mimic (left side) into FJs (L4/5 and L5/6) of rats through the joint capsule (FIG. 6A). Rats that underwent only surgical procedure without injection composed the sham group (FIG. 6B). At 3 weeks after injections, FJs were extracted and subjected to histopathology and immunohistochemistry. Histopathological analysis of Safranin O/Fast green-stained FJ sections in combination with OARSI scoring showed that miR-181a-5p mimic treatment resulted in a FJ OA-like phenotype, with significant degeneration of facet cartilage associated with loss of chondrocyte cellularity and proteoglycan depletion compared with control mimic injection (FIG. 6C-I). Immunohistochemical analysis using PARP p85 antibody as a marker of chondrocyte apoptosis further showed a significant increase in PARP p85 positive cells in miR-181a-5p mimic-treated FJs compared with control mimic-treated FJs (FIGS. 6J-L and P). Furthermore, immunohistochemical analysis using MMP13 antibody to account for cartilage catabolic activity showed significantly increased MMP13-expressing cells in miR-181a-5p mimic-treated FJs compared with control mimic-treated FJs (FIG. 6M-P). These findings show that miR-181a-5p promotes facet cartilage degeneration, chondrocyte death and catabolic activity in vivo.

The endogenous mechanisms associated with the degeneration of facet cartilage during FJ OA are largely unknown. One of the biggest hurdles in FJ OA research has been the inability to adequately identify patients with varying degrees of facet cartilage degeneration and severity. Such identification and characterization is critical for studying the true mechanisms of cartilage degeneration. To understand the endogenous mechanisms associated with facet cartilage degeneration, we first created a unique biobank of facet cartilage with varying degrees of degeneration. We sequentially assessed the degree of FJ degeneration in two clinically distinct cohorts of patients undergoing lumbar spinal surgery. MRI analysis showed that all LSS patients exhibited significantly greater FJ degeneration compared to all LDH patients. The distinct degree of FJ degeneration between the patient groups was further assessed by histological analysis using OARSI scoring. Molecular assessment of FJ cartilage revealed significantly enhanced expression of inflammatory, catabolic and cell death markers, as well as reduced expression of the major cartilage matrix molecule (COL2A1) in FJ OA compared to control facet cartilage. To our knowledge, this is the most validated cohort of patients exhibiting varying degrees of facet cartilage degeneration.

Our comprehensive characterization of lumbar facet cartilage enabled the first evaluation of miRNA expression in facet cartilage at different stages of degeneration. We identified a panel of miRNAs (out of 2,100 miRNAs screened by microarray analysis) that exhibited differential expression in FJ OA compared to control cartilage. With further validation using RT-PCR analysis of a panel of 7 miRNAs (with greater than 2-fold change in FJ OA cartilage compared to control cartilage), we identified two specific miRNAs (miR-181a-5p and miR-4454) that were significantly elevated in the FJ OA cartilage compared to control cartilage, with no significant difference in the expression of other miRNAs. Remarkably, the expression of both miR-181a-5p and miR-4454 exhibited significant, positive correlations with the severity of FJ OA based on MRI grading.

To date, no study has reported the identification of miR-181a-5p and miR-4454 in facet cartilage or up-regulation in FJ OA. However, recent studies performed in chondrocytes isolated from chicken sternal cartilage show that miR-181a reduces the expression of COL2A1 [25]. Gabler et al. showed that the expression of miR-181a is increased during hypertrophic chondrocyte differentiation in human mesenchymal stromal cells treated with transforming growth factor-beta [26]. Song et al. also reported that miR-181b, a member of the miR-181 family, was significantly up-regulated in OA chondrocytes isolated from patients with knee OA [27].

To determine if miR-181a-5p and miR-4454 play any pathophysiological role in facet cartilage degeneration, we extracted facet chondrocytes from FJ OA patients and treated these chondrocytes with miR-181a-5p or miR-4454 mimic to determine the effect of miR-181a-5p and miR-4454 mimic on the expression of major OA catabolic, inflammatory, and cell death mediators as well as the anabolic cartilage matrix molecule, type II collagen. Our results showed that miR-181a-5p mimic or miR-4454 mimic were able to significantly elevate the expression of inflammatory, catabolic and cell death markers and decrease the expression of COL2A1 compared to control mimic, suggesting that these miRNAs promote destructive mechanisms in FJ chondrocytes. Using miR-181a-5p and miR-4454 inhibitors in FJ OA chondrocytes stimulated with IL-1β, we showed that inhibition of miR-181a-5p or miR-4454 resulted in a significant suppression in the expression of inflammatory, catabolic and cell death markers and elevated the expression of COL2A1 in FJ OA chondrocytes. Consistent with our results, attenuation of miR-181b, using miR-181b inhibitor reduced MMP13 expression and increased COL2A1 expression in chondrocytes. Interestingly, over-expression of anti-miR-181b significantly reduced cartilage destruction in a mouse model of knee OA [27]. These results suggest a role for miR-181a-5p and miR-4454 as mediators of cartilage degeneration.

Since signaling mechanisms through which miR-181a-5p and miR-4454 operate in the facet cartilage has not been reported, we applied a computational biology approach and identified ten potential genes commonly regulated by both miR-181a-5p and miR-4454. Validation studies of all 10 predicted genes identified that only ZNF440 was significantly elevated by both miR-181a-5p and miR-4454 mimic in FJ OA chondrocytes. Furthermore, IL-1p mediated elevation in the expression of ZNF440 was suppressed in the presence of miR-181a-5p or miR-4454 inhibitors, suggesting a crucial role of ZNF440 in miR-181a-5p or miR-4454 signaling in FJ OA chondrocytes. IL-1p has been previously shown to activate NF-κB in human OA chondrocytes [28, 29]. Previous studies have also reported links between miR-181 and miR-4454, and NF-κB signaling in other cells and tissues. Activation of STAT3, an important component of the NF-κB signaling pathway, increases miR-181 expression in cancer cells[30], while NF-κB regulates the expression of miR-181 in breast tumor cells[31]. A study performed in TNFα-stimulated HeLa cells also identified miR-4454 as a NF-κB target miRNA[32]. Our computational approach using pathway enrichment analysis also predicted close association of the NF-κB pathway with both miR-181a-5p and miR-4454. Indeed, our results showed that FJ OA chondrocytes treated with IL-1β enhanced phosphorylation of Ser536 of NF-κB p65, which promotes NF-κB p65 activity independent of IκB expression[24], and increased the expression of miR-181a-5p and miR-4454. We found that these miRNAs alone also increased phosphorylation of Ser536 NF-κB p65 through increased expression of ZNF440, and reduced the expression of IκBα, an inhibitor of NF-κB p65 nuclear localization and activity[23]. Overall, these observations suggest that IL-1β mediated activation of NF-κB signaling may up-regulate miR-181a-5p and miR-4454 expression to sustain NF-κB activation in part through ZNF440-mediated phosphorylation of Ser536 NF-κB p65 and reduction of IκB expression, resulting in a positive feedback loop that can sustain NF-κB p65 activity. Thus, expression of miR-181a-5p and miR-4454 appears important for regulating both canonical NF-κB signaling (IκB-dependent) and the ZNF440/NF-κB axis (IκB-independent) in FJ OA chondrocytes.

Our in vitro data using miR-181a-5p and miR-4454 mimic or inhibitors strongly suggested that these miRNAs are potential mediators of facet cartilage degeneration. To prove this in vivo, we performed an intra-articular injection of miR-181a-5p mimic into L4/5 and L5/6 spinal levels in rats. At 3 weeks after injection, FJ cartilage treated with miR-181a-5p mimic exhibited a FJ OA phenotype associated with substantial cartilage degeneration, excessive loss of chondrocytes, proteoglycan depletion, enhanced chondrocyte apoptosis (PARP p85 immunostaining), and increased cartilage catabolic activity (MMP13 immunostaining). These findings further consolidate the ability of miR-181a-5p to mediate facet cartilage degeneration in vivo by promoting cell death and cartilage destructive activity and also represent a viable in vivo experimental model for FJ degeneration.

Overall, this study provides the first comprehensive evidence of miR-181a-5p and miR-4454 as potential mediators of cartilage degeneration as well as therapeutic targets to stop, reduce, delay, or otherwise counteract facet cartilage degeneration during OA, as shown in FJ OA but applicable to other body areas as listed below. The fact that both miR-181a-5p and miR-4454 are significantly elevated in FJ OA cartilage and exhibit a positive correlation with disease severity as assessed by MRI nominates these two miRNAs as markers of cartilage degeneration. Moreover, the expression of circulating miR-181a-5p and miR-4454 varies in the serum/plasma of patients with varying degrees of FJ OA (see below); this allows a comprehensive exploitation of their potential as clinical markers to detect cartilage degeneration. This study also investigated the expression and regulation of miRNAs in FJs. Expression and regulation of miR-181a-5p and miR-4454 can be evaluated in other joints or body areas affected by OA. In some embodiments, the body area is lumbar facet. In some embodiments, the body area is glenohumeral. In some embodiments, the body are is tibio-talar (ankle). In some embodiments, the body area is hip. In some embodiments, the body area is lumbar disc. In some embodiments, the body area is knee.

The fact that both miR-181a-5p and miR-4454 are significantly elevated in FJ OA cartilage and exhibit positive correlation with disease severity as assessed by MRI, shows that these two miRNAs have utility as markers of facet cartilage degeneration and in some embodiments may have utility in disc degeneration, knee OA, and hip OA.

miR-181a-5p and miR-4454 in Serum/Plasma of Patients with FJ OA

We tested the expression of circulating miR-181a-5p and miR-4454 in the serum/plasma of patients with FJ OA with varying degrees of disease severity and symptomatology to comprehensively exploit their potential as clinical markers to detect facet cartilage degeneration, ability to test symptom severity as well as therapeutic response to therapies. Plasma samples from 40 patients (FJ OA grade 0; n=9, grade 1; n=10, grade 2; n=10, grade3; n=11) were used for this experiment. All blood samples were drawn 3 months prior to spine surgeries for either microdiscectomy or decompression. Plasma was isolated from each sample and then stored in liquid nitrogen until use.

Total RNA was extracted from human plasma using the miRCURY™ RNA isolation kit—biofluids (Exiqon, Vedbaek, Denmark). Plasma was thawed on ice and centrifuged at 3000×g for 5 min in a 4° C. microcentrifuge. An aliquot of 200 μL of plasma per sample was transferred to a new microcentrifuge tube and 60 μl of Lysis solution BF (buffer) containing 1 μg carrier-RNA per 60 μl Lysis Solution BF and RNA spike-in template mixture was added to the sample. The tube was vortexed and incubated for 3 min at room temperature, followed by addition of 20 μL Protein Precipitation solution BF. The tube was vortexed, incubated for 1 min at room temperature and centrifuged at 11,000×g for 3 min. The clear supernatant was transferred to a new collection tube, and 270 μL isopropanol was added. The solutions were vortexed and transfer to a binding column. The column was incubated for 2 min at room temperature, and emptied using a vacuum-manifold. 100 μL wash solution 1 BF was added to the columns. The liquid was removed using a vacuum-manifold, and 700 μL wash solution 2 BF was added. The liquid was removed using a vacuum-manifold. 250 μl wash solution was added and the column was spun at 11.000×g to dry the columns entirely. The dry columns were transferred to a new collection tube and 50 μL RNase free H$_2$O was added directly on the membrane of the spin column. The column was incubated for 1 min at room temperature prior to centrifugation at 11,000×g. The RNA was stored in a −80° C. freezer.

2 μl RNA was reverse transcribed in 10 μl reactions using the miRCURY LNA Universal RT microRNA PCR, Polyadenylation and cDNA synthesis kit (Exiqon). cDNA was diluted 50× and assayed in 10 μl PCR reactions according to the protocol for miRCURY LNA Universal RT microRNA PCR; each microRNA was assayed once by qPCR on the microRNA Ready-to-Use PCR, Custom Pick and Mix using ExiLENT SYBR Green master mix. Negative controls excluding template from the reverse transcription reaction was performed and profiled like the samples. The amplification was performed in a LightCycler 480 Real-Time PCR System (Roche) in 384 well plates. The amplification curves were analyzed using the Roche LC software, both for determination of Cq (by the 2nd derivative method) and for melting curve analysis.

Amplification efficiency was calculated using algorithms provided by Exiqon, which produces results similar to those producible using LinReg software. Poor amplification curves are efficiently removed by applying an efficiency cutoff at >1.6. All assays were inspected for distinct melting curves and the Tm was checked to be within known specifications for the assay. Furthermore assays must be detected with 3 Cqs less than the negative control, and with Cq<37 to be included in the data analysis. Data that did not pass these criteria were omitted from any further analysis. Cq was calculated as the $2^{nd}$ derivative. Using NormFinder the best normalizer was found to be the average of assays detected in all samples. All data was normalized to the average of assays detected in all samples (average—assay Cq). Data was log-transformed prior to analysis by unpaired Students' t-tests.

Figure 8:
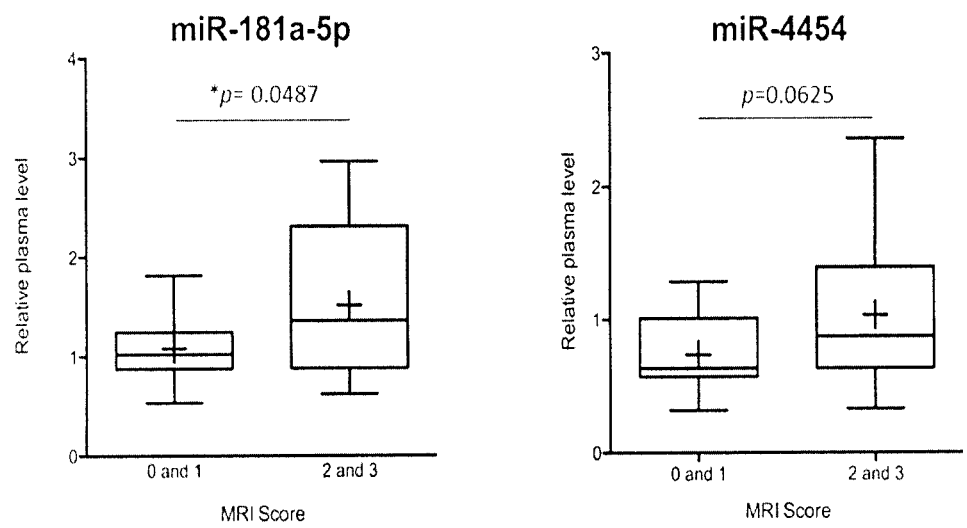
FIG. 8 shows miR-181a-5p and miR-4454 expression in human blood plasma in patients (N=40) with varying degree of FJ degeneration. *p<0.05, as determined by two-tailed Student's T-tests.

Expression of microRNAs in blood plasma from patients with MRI scores for FJ degeneration of 0, 1, 2 and 3 was measured by qPCR relative to global miRNA levels in blood plasma (FIG. 8). We observed a significant increase in the expression of miR-181a-5p and a numerical increase in the expression of miR-4454 in blood plasma of patients whose MRI scores were 2/3 (moderately to severely degenerated FJ, n=21) compared to patients with scores of 0/1 (no degeneration to mildly degenerated FJ, n=19).

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Suri, P., Hunter, D. J., Rainville, J., Guermazi, A. & Katz, J. N. Presence and extent of severe facet joint osteoarthritis are associated with back pain in older adults. *Osteoarthritis Cartilage* 21, 1199-206 (2013).
2. Miyaki, S. et al. MicroRNA-140 is expressed in differentiated human articular chondrocytes and modulates interleukin-1 responses. *Arthritis Rheum* 60, 2723-30 (2009).
3. Lee, Y., Jeon, K., Lee, J. T., Kim, S. & Kim, V. N. MicroRNA maturation: stepwise processing and subcellular localization. *Embo j* 21, 4663-70 (2002).
4. Lee, Y. et al. The nuclear RNase III Drosha initiates microRNA processing. *Nature* 425, 415-9 (2003).
5. Voinnet, O. Origin, biogenesis, and activity of plant microRNAs. *Cell* 136, 669-87 (2009).
6. Londin, E. et al. Analysis of 13 cell types reveals evidence for the expression of numerous novel primate- and tissue-specific microRNAs. 112, E1106-15 (2015).
7. Johnnidis, J. B. et al. Regulation of progenitor cell proliferation and granulocyte function by microRNA-223. *Nature* 451, 1125-9 (2008).
8. Sun, L. et al. MicroRNA-34a suppresses cell proliferation and induces apoptosis in U87 glioma stem cells. *Technol Cancer Res Treat* 11, 483-90 (2012).
9. Anderson, R. M. A role for dicer in aging and stress survival. *Cell Metab* 16, 285-6 (2012).
10. Tuddenham, L. et al. The cartilage specific microRNA-140 targets histone deacetylase 4 in mouse cells. *FEBS Lett* 580, 4214-7 (2006).
11. Miyaki, S. et al. MicroRNA-140 plays dual roles in both cartilage development and homeostasis. *Genes Dev* 24, 1173-85 (2010).
12. Tardif, G., Hum, D., Pelletier, J. P., Duval, N. & Martel-Pelletier, J. Regulation of the IGFBP-5 and MMP-13 genes by the microRNAs miR-140 and miR-27a in human osteoarthritic chondrocytes. *BMC Musculoskelet Disord* 10, 148 (2009).
13. Tardif, G. et al. NFAT3 and TGF-beta/SMAD3 regulate the expression of miR-140 in osteoarthritis. *Arthritis Res Ther* 15, R197 (2013).
14. Yamasaki, K. et al. Expression of MicroRNA-146a in osteoarthritis cartilage. *Arthritis Rheum* 60, 1035-41 (2009).
15. Li, J. et al. miR-146a, an IL-1beta responsive miRNA, induces vascular endothelial growth factor and chondrocyte apoptosis by targeting Smad4. *Arthritis Res Ther* 14, R75 (2012).
16. Beyer, C. et al. Signature of circulating microRNAs in osteoarthritis. *Ann Rheum Dis* 74, e18 (2015).
17. Weishaupt, D., Zanetti, M., Boos, N. & Hodler, J. MR imaging and CT in osteoarthritis of the lumbar facet joints. *Skeletal Radiol* 28, 215-9 (1999).
18. Pfirrmann, C. W., Metzdorf, A., Zanetti, M., Hodler, J. & Boos, N. Magnetic resonance classification of lumbar intervertebral disc degeneration. *Spine* (Phila Pa. 1976) 26, 1873-8 (2001).
19. Pritzker, K. P. et al. Osteoarthritis cartilage histopathology: grading and staging. *Osteoarthritis Cartilage* 14, 13-29 (2006).
20. Zhang, Y. et al. Cartilage-specific deletion of mTOR upregulates autophagy and protects mice from osteoarthritis. *Ann Rheum Dis* 74, 1432-40 (2015).
21. Shirdel, E. A., Xie, W., Mak, T. W. & Jurisica, I. NAViGaTing the micronome—using multiple microRNA prediction databases to identify signalling pathway-associated microRNAs. *PLoS One* 6, e17429 (2011).
22. Brown, K. R. et al. NAViGaTOR: Network Analysis, Visualization and Graphing Toronto. *Bioinformatics* 25, 3327-9 (2009).
23. Beg, A. A. et al. I kappa B interacts with the nuclear localization sequences of the subunits of NF-kappa B: a mechanism for cytoplasmic retention. *Genes Dev* 6, 1899-913 (1992).
24. Sasaki, C. Y., Barberi, T. J., Ghosh, P. & Longo, D. L. Phosphorylation of RelA/p65 on serine 536 defines an I{kappa}B{alpha}-independent NF-{kappa}B pathway. *J Biol Chem* 280, 34538-47 (2005).
25. Sumiyoshi, K. et al. Novel role of miR-181a in cartilage metabolism. *J Cell Biochem* 114, 2094-100 (2013).
26. Gabler, J. et al. Stage-Specific miRs in Chondrocyte Maturation: Differentiation-Dependent and Hypertrophy-Related miR Clusters and the miR-181 Family. *Tissue Eng Part A* (2015).
27. Song, J. et al. MicroRNA-181b regulates articular chondrocytes differentiation and cartilage integrity. *Biochem Biophys Res Commun* 431, 210-4 (2013).
28. Bauge, C. et al. Interleukin-1beta up-regulation of Smad7 via NF-kappaB activation in human chondrocytes. *Arthritis Rheum* 58, 221-6 (2008).
29. Agarwal, S. et al. Role of NF-kappaB transcription factors in antiinflammatory and proinflammatory actions of mechanical signals. *Arthritis Rheum* 50, 3541-8 (2004).
30. Iliopoulos, D., Jaeger, S. A., Hirsch, H. A., Bulyk, M. L. & Struhl, K. STAT3 activation of miR-21 and miR-181b-1 via PTEN and CYLD are part of the epigenetic switch linking inflammation to cancer. *Mol Cell* 39, 493-506 (2010).
31. Kastrati, I., Canestrari, E. & Frasor, J. PHLDA1 expression is controlled by an estrogen receptor-NFkappaB-miR-181 regulatory loop and is essential for formation of ER+ mammospheres. *Oncogene* 34, 2309-16 (2015).
32. Zhou, F. et al. NF-kappaB target microRNAs and their target genes in TNFalpha-stimulated HeLa cells. *Biochim Biophys Acta* 1839, 344-54 (2014).

The invention claimed is:

1. A method of reducing severity of osteoarthritis in a joint of a subject in need thereof, the joint selected from knee and facet, the method comprising administering to the subject an antisense oligonucleotide having at least 95% sequence identity to any one of SEQ ID NO: 3 or SEQ ID NO: 4.

2. The method of claim 1, wherein the antisense oligonucleotide is directly injected into the joint.

3. The method of claim 1, wherein the antisense oligonucleotide consists of SEQ ID NO: 3.

4. The method of claim 1, wherein the antisense oligonucleotide consists of SEQ ID NO. 4.

5. The method of claim 1, wherein the antisense oligonucleotide is two antisense oligonucleotides consisting of SEQ ID NO. 3 and SEQ ID NO. 4.

6. The method of claim 1, wherein the antisense oligonucleotide has at least 98% or 99% sequence identity to any one of SEQ ID NO: 3 or SEQ ID NO: 4.

* * * * *